United States Patent
Jiang et al.

(10) Patent No.: US 11,920,190 B2
(45) Date of Patent: Mar. 5, 2024

(54) METHOD OF AMPLIFYING AND DETERMINING TARGET NUCLEOTIDE SEQUENCE

(71) Applicant: Industrial Technology Research Institute, Hsinchu (TW)

(72) Inventors: Pei-Shin Jiang, Hsinchu (TW); Jenn-Yeh Fann, Hsinchu County (TW); Hung-Chi Chien, Hsinchu (TW); Yu-Yu Lin, Yilan County (TW); Chih-Lung Lin, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 256 days.

(21) Appl. No.: 17/134,502

(22) Filed: Dec. 28, 2020

(65) Prior Publication Data

US 2021/0214780 A1    Jul. 15, 2021

Related U.S. Application Data

(60) Provisional application No. 62/954,673, filed on Dec. 30, 2019.

(51) Int. Cl.
*C12Q 1/6855* (2018.01)
*C12Q 1/6869* (2018.01)

(52) U.S. Cl.
CPC ......... *C12Q 1/6855* (2013.01); *C12Q 1/6869* (2013.01)

(58) Field of Classification Search
None
See application file for complete search history.

(56) References Cited

U.S. PATENT DOCUMENTS

| 9,487,829 | B2 | 11/2016 | Vogelstein et al. |
| 9,747,414 | B2 | 8/2017 | Pan et al. |
| 10,385,387 | B2 | 8/2019 | Lee et al. |
| 2017/0073748 | A1 | 3/2017 | Lizardi et al. |
| 2018/0100145 | A1 | 4/2018 | Lau et al. |
| 2018/0148757 | A1 | 5/2018 | Mitra et al. |

(Continued)

FOREIGN PATENT DOCUMENTS

| CN | 106103743 | 11/2016 |
| CN | 106192019 | 12/2016 |
| CN | 108220392 | 6/2018 |

(Continued)

OTHER PUBLICATIONS

"Office Action of Taiwan Counterpart Application", dated Dec. 23, 2021, p. 1-p. 7.

(Continued)

*Primary Examiner* — Kaijiang Zhang
(74) *Attorney, Agent, or Firm* — JCIPRNET

(57) ABSTRACT

Methods of amplifying and determining a target nucleotide sequence are provided. The method of amplifying the target nucleotide sequence includes the following steps. A first adaptor and a second adaptor are linked to two ends of a double-stranded nucleic acid molecule with a target nucleotide sequence respectively to form a nucleic acid template, in which the first adaptor includes a Y-form adaptor or a hairpin adaptor and the second adaptor is a hairpin adaptor. Then, a PCR amplification cycle is performed on the nucleic acid template to obtain a PCR amplicon of the target nucleotide sequence.

20 Claims, 12 Drawing Sheets

Specification includes a Sequence Listing.

(56) References Cited

U.S. PATENT DOCUMENTS

2018/0187257 A1     7/2018   Soper et al.
2019/0177776 A1     6/2019   Coll Mulet et al.

FOREIGN PATENT DOCUMENTS

| EP | 3098324 | | 11/2016 | | |
|---|---|---|---|---|---|
| TW | I385253 | | 2/2013 | | |
| TW | 202124728 | | 7/2021 | | |
| WO | WO-2015104302 | A1 * | 7/2015 | ............ | C07H 21/04 |
| WO | 2018104908 | | 6/2018 | | |
| WO | 2019183640 | | 9/2019 | | |
| WO | 2019209946 | | 10/2019 | | |
| WO | 2021032060 | | 2/2021 | | |

OTHER PUBLICATIONS

Mark T Gregory et al., "Targeted single molecule mutation detection with massively parallel sequencing," Nucleic Acids Res., vol. 44, No. 3, Feb. 18, 2016, pp. 1-11.
Joseph B Hiatt et al., "Single molecule molecular inversion probes for targeted, high-accuracy detection of low-frequency variation," Genome Res., vol. 23, No. 5, May 2013, pp. 843-854.
Isaac Kinde et al., "Detection and quantification of rare mutations with massively parallel sequencing," PNAS, vol. 108, No. 23, Jun. 7, 2011, pp. 9530-9535.
James A. Casbon et al., "A method for counting PCR template molecules with application to next-generation sequencing," Nucleic Acids Res., vol. 39, No. 12, Jul. 2011, pp. 1-8.
Michael W. Schmitt et al., "Detection of ultra-rare mutations by next-generation sequencing," PNAS, vol. 109, No. 36, Sep. 4, 2012, pp. 14508-14513.
Jacob Porter et al., "Investigating bisulfite short-read mapping failure with hairpin bisulfite sequencing data," BMC Genomics, vol. 16, Supplement 11, Article No. S2, Nov. 10, 2015, pp. 1-9.
Lei Zhao et al., "The dynamics of DNA methylation fidelity during mouse embryonic stem cell self-renewal and differentiation," Genome Res., vol. 24, No. 8, Aug. 2014, pp. 1296-1307.
Dianne I Lou et al., "High-throughput DNA sequencing errors are reduced by orders of magnitude using circle sequencing," PNAS, vol. 110, No. 49, Dec. 3, 2013, pp. 19872-19877.
Stefan Kirsch et al., "Sequence error storms and the landscape of mutations in cancer," PNAS, vol. 109, No. 36, Sep. 4, 2012, pp. 14289-14290.
Cassandra B Jabara et al., "Accurate sampling and deep sequencing of the HIV-1 protease gene using a Primer ID," PNAS, vol. 108, No. 50, Dec. 13, 2011, pp. 20166-20171.
Isaac Kinde et al., "Evaluation of DNA from the Papanicolaou test to detect ovarian and endometrial cancers," Sci Transl Med., vol. 5, No. 167, Jan. 9, 2013, pp. 1-21.
Scott R Kennedy et al., "Detecting ultralow-frequency mutations by Duplex Sequencing," Nature Protocols, vol. 9, No. 11, Oct. 9, 2014, pp. 2586-2606.
Joseph B Hiatt et al., "Parallel, tag-directed assembly of locally derived short sequence reads," Nature Methods, vol. 7, No. 2, Feb. 2010, pp. 1-14.
Ashley Acevedo et al., "Mutational and fitness landscapes of an RNA virus revealed through population sequencing," Nature, vol. 505, No. 7485, Jan. 30, 2014, pp. 1-34.
"Search Report of Europe Counterpart Application", dated May 28, 2021, p. 1-p. 9.
"Office Action of Europe Counterpart Application", dated Mar. 22, 2023, p. 1-p.5.

* cited by examiner

SEQ ID NO: 8  AGATGAGAAAGAAAGAGTAGCCCACagagctcgaattcAAGGTACTCGTCCTGTATCTACA  60
SEQ ID NO: 9  AGATGAGAAAGAAAGAGTAGCcAcAgagttttgaatttAAGGTATTCGTGTTGTATTTATA  60
              *********************▲*▲**** * *** **** *▲* *  *

SEQ ID NO: 8  ACTGACCGACCTGCGTCCTGACACCCCAAAACCCGCCACTTTTCCCCTTAAGAGAGTAAA  120
SEQ ID NO: 9  ATTGACCGAGTTCGGTGTTGATATTTTAAAACGICGTATTTTTTTTTTAAGAGAGTAAA  120
              * ****** ** * *      ****** ▲* * **    ************

SEQ ID NO: 8  CTTGTTTCGAAGCCAGACgatcctctagagtctctcgcgcccccttgcctcatctctaga  180
SEQ ID NO: 9  TTTGTTTCGAAGGTACAGgattttttagagttttttgtgtttttttgttttattttaga  180
              ****▲* ***** * ****** * * * *    *** * ** * ****

SEQ ID NO: 8  ggatccTCTCCCTTCGAAACAAGTTTACTCTCTCTTAAGCCGAAAAGTGCCGCCTTTTGCCG  240
SEQ ID NO: 9  ggatttTTTGTTTTTGAAATAAGTTTATTTTTTTAAGCCGAAAAGTGTCGTTTTTTGCCG  240
              ****  *    ** ***** * * **************  ********

SEQ ID NO: 8  TGTCACCACCCACCTCCCTCAGTTGTAGATACAGCACGAGTACCTTgaattcgagctcTT  300
SEQ ID NO: 9  TGTTAGTATTTAGTTTTTTTAGTTGTAGATATAGTATGAGTATTTTgaatttgagttcTT  300
              *  *  ** *  * ********  * *** * ▲

SEQ ID NO: 8  CCAAAATTGCCCAAACCGCTATAG  323
SEQ ID NO: 9  ccAAAATTGCcCAAACCGcTATAG  323
              ▲▲*****▲▲***▲***

FIG. 7

```
SEQ ID NO: 8   AGATGAGAAAGAAAGAGTACCCACAgagctcgaattcAACGTACTCGTCCTGTATCTACA 60
SEQ ID NO: 9   AGATGAGAAAGAAAGAGTACCcAcAgagttttgaatttAACGTATTcGTGTTGTATTTATA 60
SEQ ID NO: 10  TTTTTAGAAACGAAGAGTACCCCCCGAGTTTGAATTTAACGTATTCGTGTTGTATTTATA 60
                 * ****** ********** * *** * ***** ****** ***** ***** ** *

SEQ ID NO: 8   ACTGACGGAGCTCGGTCCTGACACCCCAAAACCCGCCACTTTTCCCCTTAAGAGAGTAAA 120
SEQ ID NO: 9   ATTGACGGAGTTCGGTGTTGATATTTTAAAACGTcGTATTTTTTTTTTAAGAGAGTAAA 120
SEQ ID NO: 10  ATTGACGGAGTTCGGTGTTGATATTTTAAAACGTCGTATTTTTTTTTTAAGAGAGTAAA 120
                 * ******** ****** *** *      ****** ** * ****    *************

SEQ ID NO: 8   CTTGTTTCGAACCCAGACgatcctctagagtctctcgcgccccctTgcctcatctctaga 180
SEQ ID NO: 9   TTTGTTTcGAACGTAGAGgattttttagagttttttgtgttttttTgttttattttaga 180
SEQ ID NO: 10  TTTGTTTCGAACGTAGACGATTTTTTAGAGTTTTTTGTGTTTTTTTGTTTATTTTAGA 180
                 ************ ******* * ****** * * * *    *** * ** * ****

SEQ ID NO: 8   ggatccTCTCCCTTCCGAAACAAGTTTACTCTCTTAACCCGAAAAGTCCCCCCTTTTCCCG 240
SEQ ID NO: 9   ggatttTTTGTTTTTGAAATAAGTTTATTTTTTTAACCCGAAAAGTGTCGTTTTTTCCCG 240
SEQ ID NO: 10  CGATTTTTTGTTTTTGAAATAAGTTTATTTTTTTAACCCGAAAAGTGTCGTTTTTTCCCG 240
                 ****  * ** ** **** ******* * ****************** ** *********

SEQ ID NO: 8   TGTCACCACCCACCTCCCTCAGTTGTAGATACACCACGAGTACCTTgaattcgagctcTT 300
SEQ ID NO: 9   TGTTAGTATTTAGTTTTTTTAGTTGTAGATATAGTATGAGTATTTTgaatttgagttcTT 300
SEQ ID NO: 10  TGTTAGTATTTAGTTTTTTTAGTTGTAGATATAGTATGAGTATTTGAATTTCCTGT---- 296
                 *** ** *  ** *  * *********** ** *****  *  **       *

SEQ ID NO: 8   CCAAAATTCCCCAAACCCTATAG       323
SEQ ID NO: 9   ccAAAATTCCcAAACCcTATAG        323
SEQ ID NO: 10  ----------------------        296
```

| | | |
|---|---|---|
| SEQ ID NO: 9 | AGATGAGAAAGAAAGAGTAGGcAcAgagtttgaatttAAGGTATTGTGTTGTATTTATA | 60 |
| SEQ ID NO: 12 | CTATAgCCTTTggCCAATTTTggAAgaactcaaattcAAAATACTCATACTATATCTACA | 60 |
| SEQ ID NO: 13 | ------------------------GAGGGCTTGATTTAGGTATTGTGTTGTATTTATA | 35 |
| SEQ ID NO: 14 | ------------------------ACAGCAAATTCAAATACTCATACTATATCTACA | 33 |
| |     *  *  ** * *  * *** ** * | |
| SEQ ID NO: 9 | ATTGAGGGAGTTGGGTGTTGATATTTTAAAAGGTGTATTTTTTTTTTAAGAGAGTAAA | 120 |
| SEQ ID NO: 12 | ACTAAAAAAACTAAATACTAACACCCCAAAAAACCACTTTTCCCCTTAAAAAAATAAA | 120 |
| SEQ ID NO: 13 | ATTGAGGGAGTTGGGTGTTGATATTTTAAAGGTCGTATTTTTTTTTTAAAAAAGTAAA | 95 |
| SEQ ID NO: 14 | ACTAAAAAAACTAAATACTAACACCCCAAAAAACCACTTTTCCCCTTAAAAAAATAAA | 93 |
| | ***  *  * * ***   ****  * ****   **** * * **** | |
| SEQ ID NO: 9 | TTTGTTTCGAAGGTAGAGgattttttagagttttttgtgttttttgttttattttaga | 180 |
| SEQ ID NO: 12 | CTTATTTCAAAAACAAAaaatcctctaaaaataaaacaaaaaaacacaaaaaactctaaa | 180 |
| SEQ ID NO: 13 | TTTGTTTCGAAGGTAAAGGATTTTTTAAAGTTTTTTGTGTTTTTTTGTTTTATTTTTAAA | 155 |
| SEQ ID NO: 14 | CTTATTTCAAAAACAAAAAAATCCTCTAAAAATAAAACAAAAAAACACAAAAAACTCTAAA | 153 |
| | ** **** **  * * ** * ** * *       *  * ** * | |
| SEQ ID NO: 9 | ggattTTTGTTTTTGAAATAAGTTTATTTTTTTAAGGGGAAAAGTGTGGTTTTTGGGG | 240 |
| SEQ ID NO: 12 | aaatcCTCTACCTTCgAAACAAATTTACTCTCTTAAAAAAAAAAATACgACCTTTTAAAA | 240 |
| SEQ ID NO: 13 | GGATTTTTTGTTTTGAAATAATTTTATTTTTTTAAGGGAAAAGGGGGGTTTTTGGGGG | 215 |
| OSEQ ID NO: 14 | AAATCCTCTACCTTCGAAACAAATTTACTCTCTTAAAAAAAAAAAATACGACCTTTTAAAA | 213 |
| | **  * *  ** **** ** **** * * ****  ****  *  *** | |
| SEQ ID NO: 9 | TGTTAGTATTTAGTTTTTTTAGTTGTAGATATAGTATGAGTATTTTgaatttgagttcTT | 300 |
| SEQ ID NO: 12 | TATCAACACCCAACTCCCTCAATTATAAATACAACACgAATACCTTaaattcaaactcTg | 300 |
| SEQ ID NO: 13 | GGTTAGTATTTATTTTTTTTAGTTGAAAATATAGAATGAGTATTTTGAATTTGATTTCTT | 275 |
| SEQ ID NO: 14 | TATCAACACCCAACTCCCTCAATTATAAATACAACACGAATACCTTAAATTCAAACTCGG | 273 |
| | *  * *  *  *  * *** * *** * * ** ** ** **** *  ** | |
| SEQ ID NO: 9 | ccAAAATTGGccAAAGGcTATAG- | 323 |
| SEQ ID NO: 12 | TgCCTACTCTTTCTTTCTCATCT- | 323 |
| SEQ ID NO: 13 | CCAAAATTGGCCAAAGGCTAAAAA | 299 |
| SEQ ID NO: 14 | GGCCTACTCTTCCTTTCTAAAAA- | 296 |
| |   **        * | |

FIG. 12

SEQUENCE LISTING

```
<160> NUMBER OF SEQ ID NOS: 14

<210> SEQ ID NO 1
<211> LENGTH: 12
<212> TYPE: DNA
<213> ORGANISM: Artificial Sequence
<220> FEATURE:
<223> OTHER INFORMATION: Synthetic

<400> SEQUENCE: 1
gagctcgaat tc                                                          12

<210> SEQ ID NO 2
<211> LENGTH: 12
<212> TYPE: DNA
<213> ORGANISM: Artificial Sequence
<220> FEATURE:
<223> OTHER INFORMATION: Synthetic

<400> SEQUENCE: 2
ggatcctcta ga                                                          12

<210> SEQ ID NO 3
<211> LENGTH: 100
<212> TYPE: DNA
<213> ORGANISM: Artificial Sequence
<220> FEATURE:
<223> OTHER INFORMATION: Synthetic

<400> SEQUENCE: 3
```

```
aaggtactcg tgctgtatct acaactgagg gagctgggtg ctgacacccc aaaaggccgc      60
acttttcccc ttaagagagt aaacttgttt cgaaggcaga                          100

<210> SEQ ID NO 4
<211> LENGTH: 186
<212> TYPE: DNA
<213> ORGANISM: Artificial Sequence
<220> FEATURE:
<223> OTHER INFORMATION: Synthetic

<400> SEQUENCE: 4
agatgagaaa gaaagagtag gcacagagct cgaattcaag gtactcgtgc tgtatctaca      60
actgagggag ctgggtgctg acaccccaaa aggccgcact tttcccctta agagagtaaa     120
cttgtttcga aggcagagga tcctctagag tctctcgcgc ccccttgcct catctctaga     180
ggatcc                                                               186

<210> SEQ ID NO 5
<211> LENGTH: 137
<212> TYPE: DNA
<213> ORGANISM: Artificial Sequence
<220> FEATURE:
<223> OTHER INFORMATION: Synthetic

<400> SEQUENCE: 5
tctgccttcg aaacaagttt actctcttaa ggggaaaagt gcggcctttt ggggtgtcag      60
cacccagctc cctcagttgt agatacagca cgagtacctt gaattcgagc tcttccaaaa     120
ttggccaaag gctatag                                                   137

<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
atgagaaaga aagagtaggc acaga                                           25

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
tatagccttt ggccaatttt ggaag                                           25

<210> SEQ ID NO 8
<211> LENGTH: 323
<212> TYPE: DNA
<213> ORGANISM: Artificial Sequence
<220> FEATURE:
<223> OTHER INFORMATION: Synthetic

<400> SEQUENCE: 8
agatgagaaa gaaagagtag gcacagagct cgaattcaag gtactcgtgc tgtatctaca      60
actgagggag ctgggtgctg acaccccaaa aggccgcact tttcccctta agagagtaaa     120
cttgtttcga aggcagagga tcctctagag tctctcgcgc ccccttgcct catctctaga     180
```

```
ggatcctctg ccttcgaaac aagtttactc tcttaagggg aaaagtgcgg ccttttgggg      240
tgtcagcacc cagctccctc agttgtagat acagcacgag taccttgaat tcgagctctt      300
ccaaaattgg ccaaaggcta tag                                              323
```

<210> SEQ ID NO 9
<211> LENGTH: 323
<212> TYPE: DNA
<213> ORGANISM: Artificial Sequence
<220> FEATURE:
<223> OTHER INFORMATION: Synthetic

<400> SEQUENCE: 9

```
agatgagaaa gaaagagtag gcacagagtt tgaatttaag gtattcgtgt tgtatttata       60
attgagggag ttgggtgttg atattttaaa aggtcgtatt ttttttttta agagagtaaa      120
tttgtttcga aggtagagga ttttttagag tttttttgtgt tttttttgttt tattttttaga   180 ggatttttttg ttttttgaaat aagtttattt ttttaagggg aaaagtgtgg ttttttgggg    240
tgttagtatt tagttttttt agttgtagat atagtatgag tatttttgaat ttgagttctt    300 ccaaaattgg ccaaaggcta tag                                              323
```

<210> SEQ ID NO 10
<211> LENGTH: 296
<212> TYPE: DNA
<213> ORGANISM: Artificial Sequence
<220> FEATURE:
<223> OTHER INFORMATION: Synthetic

<400> SEQUENCE: 10

```
tttttagaaa ggaagagtag gccccgagtt tgaatttaag gtattcgtgt tgtatttata       60
attgagggag ttgggtgttg atattttaaa aggtcgtatt ttttttttta agagagtaaa     120
tttgtttcga aggtagagga tttttttagag tttttttgtgt tttttttgttt tattttttaga  180 ggattttttg ttttttgaaat aagtttattt ttttaagggg aaaagtgtgg ttttttgggg    240
tgttagtatt tagttttttt agttgtagat atagtatgag tatttgaatt tgctgt         296
```

<210> SEQ ID NO 11
<211> LENGTH: 323
<212> TYPE: DNA
<213> ORGANISM: Artificial Sequence
<220> FEATURE:
<223> OTHER INFORMATION: Synthetic

<400> SEQUENCE: 11

```
ctatagcctt tggccaattt tggaagagct cgaattcaag gtactcgtgc tgtatctaca       60
actgagggag ctgggtgctg acaccccaaa aggccgcact tttcccctta agagagtaaa     120
cttgtttcga aggcagagga tcctctagag atgaggcaag ggggcgcgag agactctaga    180
ggatcctctg ccttcgaaac aagtttactc tcttaagggg aaaagtgcgg ccttttgggg      240
tgtcagcacc cagctccctc agttgtagat acagcacgag taccttgaat tcgagctctg    300
tgcctactct ttctttctca tct                                              323
```

<210> SEQ ID NO 12
<211> LENGTH: 323
<212> TYPE: DNA
<213> ORGANISM: Artificial Sequence
<220> FEATURE:
<223> OTHER INFORMATION: Synthetic

<400> SEQUENCE: 12

-continued

```
ctatagcctt tggccaattt tggaagaact caaattcaaa atactcatac tatatctaca    60
actaaaaaaa ctaaatacta acaccccaaa aaaccacact tttcccctta aaaaaataaa   120
cttatttcaa aaacaaaaaa tcctctaaaa ataaaacaaa aaaacacaaa aaactctaaa   180
aaatcctcta ccttcgaaac aaatttactc tcttaaaaaa aaaaatacga ccttttaaaa   240
tatcaacacc caactccctc aattataaat acaacacgaa taccttaaat tcaaactctg   300
tgcctactct ttctttctca tct                                           323
```

<210> SEQ ID NO 13
<211> LENGTH: 299
<212> TYPE: DNA
<213> ORGANISM: Artificial Sequence
<220> FEATURE:
<223> OTHER INFORMATION: Synthetic

<400> SEQUENCE: 13

```
gagggcttga tttaggtatt cgtgttgtat ttataattga gggagttggg tgttgatatt    60
ttaaaaggtc gtattttttt ttttaaaaaa gtaaatttgt ttcgaaggta aaggattttt   120
taaagttttt tgtgttttt tgttttattt ttaaaggatt ttttgttttt gaaataattt    180
tattttttta agggaaaaag gggggttttt gggggggtta gtatttattt tttttagttg   240
aaaatataga atgagtattt tgaatttgat ttcttccaaa attggccaaa ggctaaaaa    299
```

<210> SEQ ID NO 14
<211> LENGTH: 296
<212> TYPE: DNA
<213> ORGANISM: Artificial Sequence
<220> FEATURE:
<223> OTHER INFORMATION: Synthetic

<400> SEQUENCE: 14

```
acagcaaatt caaatactca tactatatct acaactaaaa aaactaaata ctaacacccc    60
aaaaaaccac acttttcccc ttaaaaaaat aaacttattt caaaaacaaa aaatcctcta   120
aaaataaaac aaaaaaacac aaaaaactct aaaaaatcct ctaccttcga aacaaattta   180
ctctcttaaa aaaaaaaata cgaccttta aaatatcaac acccaactcc ctcaattata   240
aatacaacac gaataccta aattcaaact cggggcctac tcttcctttc taaaaa        296
```

METHOD OF AMPLIFYING AND DETERMINING TARGET NUCLEOTIDE SEQUENCE

CROSS-REFERENCE TO RELATED APPLICATION

This application claims the priority benefit of U.S. Provisional Application No. 62/954,673, filed on Dec. 30, 2019. The entirety of the above-mentioned patent application is hereby incorporated by reference herein and made a part of this specification.

TECHNICAL FIELD

The disclosure relates to a method of genomics, and particularly relates to a method of amplifying and determining a target nucleotide sequence.

BACKGROUND

After more than ten years of technological development, the cost of next-generation sequencing (NGS) is greatly reduced, and coupled with the rapid evolution of big data analysis capabilities, many countries have greatly promoted precision medicine, from which huge business opportunities have gradually emerged. In precision medicine, "early detection of changes in disease" is an important basis and indicator for diagnosis and treatment. Particularly in the development of cancer, DNA mutations may cause drug resistance and other conditions that are counterproductive to patients. Therefore, if detection may be made at an early stage, it may help the medical team take the best treatment measures for the patient.

For example, among about 20,000 genes in the human body, roughly between 300 and 400 genes are highly related to cancer. Patients suffering from the same type of cancer have different gene mutations. Therefore, even in the same cancer stage, the effect of administering the same drug is quite different. If a method similar to "comprehensive genomic profiling" may be used to detect 300 genes at a time regardless of cancer, finding out all the mutations at once and matching the patient with a suitable treatment plan may be expected to effectively save valuable time and money. In addition, instead of distinguishing by the type and stage of cancer, the gene mutations are examined and treatment is provided. This is also the spirit of "precision medicine."

However, the error rate of traditional NGS is about 1%, which may be as low as 0.1% in the best case scenario, but it still may not meet the requirement of "detecting low-frequency variant genes". Therefore, the development of a more accurate NGS method is still an important issue in the field of precision medicine.

SUMMARY

The disclosure provides a method of amplifying a target nucleotide sequence, wherein the resulting amplicon has a forward target nucleotide sequence and a reverse target nucleotide sequence in any strand.

The disclosure provides a method of determining a target nucleotide sequence that may obtain the sequence information of two complementary strands of DNA.

The disclosure provides a method of amplifying a target nucleotide sequence including the following steps. (a) A first adaptor and a second adaptor are performed to link to two ends of a double-stranded nucleic acid molecule with a target nucleotide sequence respectively to form a nucleic acid template, wherein the target nucleotide sequence includes a forward strand and a reverse strand, the first adaptor includes a Y-form adaptor or a hairpin adaptor, and the second adaptor is a hairpin adaptor. (b) Denaturation reaction on the nucleic acid template is performed. (c) A first primer, a second primer, and a DNA polymerase are brought in contact with the nucleic acid template under the conditions sufficient for a PCR amplification of the target nucleotide sequence, wherein the first primer includes a first sequence identical to a sequence of a single-strand portion of the first adaptor near the forward strand, and the second primer includes a second sequence complementary to a sequence of a single-strand portion of the first adaptor near the reverse strand. (d) Step (c) is repeated to perform one or a plurality of PCR amplification cycles to obtain a PCR amplicon of the target nucleotide sequence.

The disclosure provides a method of determining a target nucleotide sequence including the following steps. The PCR amplicon of the target nucleotide sequence obtained by the method of amplifying a target nucleotide sequence is provided. A nucleic acid sequencing is performed on the PCR amplicon of the target nucleotide sequence to obtain a sequence information of the target nucleotide sequence.

Based on the above, in the disclosure, two complementary strands of DNA (i.e., forward strand and reverse strand) of the target nucleotide sequence are held together by the hairpin second adaptor and used as a nucleic acid template, and PCR amplification cycles are performed on the nucleic acid template using primers located on the first adaptor. Therefore, any strand of the resulting PCR amplicon has a forward target nucleotide sequence and a reverse target nucleotide sequence. In addition, since any strand of the PCR amplicon includes a forward target nucleotide sequence and a reverse target nucleotide sequence, during nucleic acid sequencing analysis, the sequences of two complementary strands of DNA regions may be obtained by sequencing from either end, and the sequences of the resulting two complementary strands of DNA regions may be aligned with each other, thereby improving the accuracy of the original target nucleotide sequence. In addition, in the disclosure, two complementary strands of DNA are held together for sequencing and analysis, so the cost of sequencing may be reduced.

BRIEF DESCRIPTION OF THE DRAWINGS

FIG. 7 shows the nucleotide sequence alignment of SEQ ID NO: 8 and SEQ ID NO: 9.

FIG. 8 shows the nucleotide sequence alignment of SEQ ID NO: 8, SEQ ID NO: 9, and SEQ ID NO: 10.

FIG. 9 shows the sequence alignment of the forward sequence of a designed hairpin construct and the reverse complementary sequence thereof.

FIG. 10 shows the sequence alignment of the forward sequence of an in silico bisulfate-converted hairpin construct and the reverse complementary sequence thereof.

FIG. 12 shows the sequence alignment of SEQ ID NO: 9, SEQ ID NO: 12, SEQ ID NO: 13, and SEQ ID NO: 14.

DETAILED DESCRIPTION OF DISCLOSED EMBODIMENTS

Definition of Terms

Figure 1:
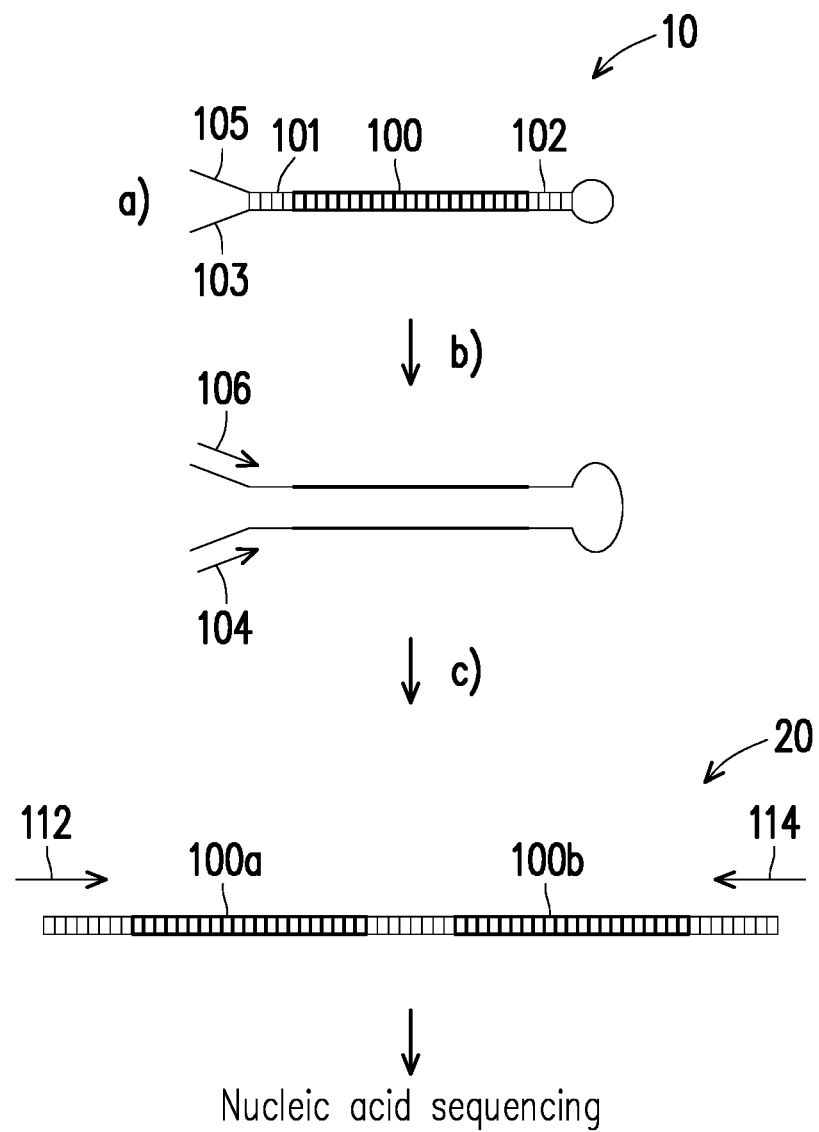
FIG. 1 is a flowchart of a method of amplifying a target nucleotide sequence according to the first embodiment of the disclosure.

In the present embodiment, a "polynucleotide" or a "nucleic acid" used interchangeably refers to a nucleotide polymer of any length, and includes DNA and RNA. A nucleotide may be a deoxyribonucleotide, a ribonucleotide, a modified nucleotide, or a base and/or an analog thereof, or any matrix that may be incorporated into a polymer by DNA or RNA polymerase. A polynucleotide may include a modified nucleotide, such as a methylated nucleotide and an analog thereof.

In the present embodiment, an "oligonucleotide" generally refers to a shorter, single-stranded, synthetic polynucleotide, with a length generally not exceeding about 200 nucleotides, but the disclosure is not limited thereto. In the present embodiment, the terms "oligonucleotide" and "polynucleotide" are not mutually exclusive. The above description of a polynucleotide is equally and fully applicable to an oligonucleotide.

The terms "5'" and "3'" usually refer to the directional two ends of the same polynucleotide or oligonucleotide in a polynucleotide or oligonucleotide. Generally, 5' is located upstream and 3' is located downstream, and a nucleotide in vivo is synthesized in the 5' to 3' direction.

In the present embodiment, the interchangeable terms "hybridization" and "annealing" mean that two nucleic acid molecules must have a high degree of homogeneity between each other (homology), so that a complex is stabilized by hydrogen bonds between the bases of a nucleotide group. In the present embodiment, a part of a nucleic acid molecule may be specifically hybridized with or annealed to a complementary sequence on another nucleic acid molecule. For example, there may be a fragment of an unhybridized nucleotide at the 5'-end of a nucleic acid molecule, and a fragment of a sequence at the 3'-end of the same nucleic acid molecule is specifically hybridized with or annealed to another nucleic acid molecule.

In the present embodiment, a "nucleic acid template" refers to a polynucleotide in a nucleic acid sample that is a starting material for target enrichment and sequencing. The nucleic acid template may be single-stranded or double-stranded.

In the present embodiment, "denaturation" refers to performing a treatment on a nucleic acid template so that a complementary double-stranded nucleic acid molecule is divided into single-stranded nucleic acid molecules, which may be used for annealing to oligonucleotide primers (such as a first primer and a second primer), etc.

In the present embodiment, a "primer" is usually a shorter single-stranded polynucleotide, and usually has a free 3'-OH group. The primer binds to a target of interest by hybridizing with a target sequence, and then promotes the polymerization of a polynucleotide complementary to the target.

In the present embodiment, a "sequencing primer" is an oligonucleotide that may be linked to a position in a nucleic acid molecule suitable for primer ligation and extension in a sequencing reaction to generate sequence information.

In the present embodiment, an "adaptor" refers to an oligonucleotide that may be linked to a polynucleotide fragment.

"Melting temperature" refers to the temperature at which half of a nucleic acid is in an untwisted state in the solution, and the other half of the nucleic acid is in a twisted state. When the adaptors may form hairpins, the melting temperature is the temperature at which half of the adaptors are partially self-hybridized "hairpins".

When a nucleic acid adaptor and a nucleic acid sample have no other inserted repeated sequences between the nucleic acid adaptor and the nucleic acid sample, the nucleic acid adaptor and the nucleic acid sample are immediately upstream or downstream of each other. In a single-stranded molecule, upstream means the 5'-end direction, and downstream means the 3'-end direction. In a double-stranded molecule, this polarity may be determined by itself or may be determined based on the polarity of directional constituent elements (such as a promoter, a coding sequence, etc.) For example, the polarity of a promoter is extended downstream from the direction in which RNA polymerase starts to synthesize. The polarity of a coding sequence is extended downstream from the start codon to the direction of the stop codon.

In the present embodiment, "amplification" refers to the process of producing two or more copies of a desired sequence. The components of the amplification reaction may include a primer, a nucleic acid template, a polymerase, a nucleotide, and a dNTP, but the disclosure is not limited thereto.

"Product of amplification", "amplified product", or "amplicon" refers to an oligonucleotide produced by a PCR amplification reaction and is a copy of a part of a specific target template nucleic acid and/or the complementary sequence thereof, which corresponds to a nucleic acid template sequence and/or the complementary sequence thereof in a nucleotide sequence. The amplified product may further include a sequence specific to a primer, and the sequence flanks the sequence of a target nucleic acid and/or the complementary sequence thereof. An amplicon as described herein is usually a double-stranded DNA, but may also be cited as a single-stranded DNA.

The term "enrichment" refers to a process of increasing the relative abundance of a specific nucleic acid sequence in a sample relative to the level of the overall nucleic acid sequence initially present in the sample before treatment. Therefore, the enrichment step provides a relative percentage or fraction increase, rather than a direct increase. After the enrichment step, the sample to be analyzed may be referred to as an enriched or selected polynucleotide.

The disclosure provides a method of amplifying a target nucleotide sequence that may effectively perform target sequence enrichment on a target sequence. Specifically, the disclosure provides a method of enriching a target nucleotide sequence of interest before using next-generation sequencing techniques to determine the target nucleotide sequence.

The disclosure provides a method of amplifying a target nucleotide sequence including the following steps: (a) a first adaptor and a second adaptor are linked to two ends of a double-stranded nucleic acid molecule with a target nucleotide sequence respectively to form a nucleic acid template, wherein the target nucleotide sequence includes a forward strand and a reverse strand, the first adaptor includes a Y-form adaptor or a hairpin adaptor, and the second adaptor is a hairpin adaptor; (b) a denaturation reaction is performed on the nucleic acid template; (c) a PCR amplification is performed on the target nucleotide sequence, so that a first primer, a second primer, and a DNA polymerase are in contact with the nucleic acid template, wherein the first primer includes a first sequence identical to a sequence of a single-strand portion of the first adaptor near the forward strand, and the second primer includes a second sequence complementary to a sequence of a single-strand portion of the first adaptor near the reverse strand; and (d) step (c) is repeated to perform one or a plurality of PCR amplification cycles to obtain a PCR amplicon of the target nucleotide sequence.

In the present embodiment, the target nucleotide sequence refers to the sequence of a double-stranded target polynucleotide that may include a forward strand and a reverse strand.

In the present embodiment, the adaptor used includes a first adaptor and a second adaptor, wherein the first adaptor includes a Y-form adaptor or a hairpin adaptor, and the second adaptor is a hairpin adaptor.

In an embodiment, the Y-form adaptor includes a paired double-stranded part and an unpaired single-stranded part. Specifically, the Y-form adaptor includes a linkable double-stranded part at the first end, and includes an oligonucleotide of a non-double-stranded part at the second end, wherein the double-stranded part may be linked to a double-stranded nucleic acid molecule with the target nucleotide sequence. In an embodiment, the Y-form adaptor includes a separate first strand and second strand, wherein the first strand of the Y-form adaptor refers to a strand for which the 3'-end is located at the first end (i.e., linkable end) of the Y-form adaptor. The second strand of the Y-form adaptor refers to the other strand for which the 5'-end is located at the first end (i.e., linkable end) of the Y-form adaptor.

In an embodiment, the first strand of the Y-form adaptor includes a 5' unpaired part and a 3' paired part, and the second strand of the Y-form adaptor has a 3' unpaired part and a 5' paired part. In an embodiment, the pairing parts of the first strand and the second strand of the Y-form adaptor are substantially complementary and form a first end including a linkable double-stranded part, and the double-stranded part has a sufficient length to maintain the double-stranded form at the annealing temperature.

In an embodiment, the non-double-strand part of the Y-form adaptor includes a first unpaired strand (for example, the 5' unpaired part of the first strand) and a second unpaired strand (the 3' unpaired part of the second strand). In an embodiment, the length of the first unpaired strand of the Y-form adaptor may be shorter, longer, or equal to the length of the second unpaired strand.

In an embodiment, the first unpaired strand and the second unpaired strand of the Y-form adaptor are substantially not complementary. In an embodiment, the second unpaired strand (i.e., the 3' unpaired part) of the second strand of the Y-form adaptor is not specifically annealing to the first unpaired strand of the first strand (i.e., the 5' unpaired part) at the annealing temperature.

In an embodiment, the length of the double-stranded part of the Y-form adaptor may be about 10 bp to 30 bp, such as about 12 bp to 28 bp, about 15 bp to 25 bp, about 18 bp, about 20 bp, etc., but is not limited thereto. In an embodiment, the length of the first unpaired strand and the second unpaired strand of the Y-form adaptor may be about 10 bp to 60 bp, such as about 15 bp to 45 bp, about 20 bp to 40 bp, about 25 bp, about 30 bp, about 35 bp, etc., but is not limited thereto. In an embodiment, the melting temperature of the Y-form adaptor may be about 30° C. to 90° C., such as about 35° C. to 90° C., about 45° C. to 85° C., about 50° C. to 80° C., about 55° C. to 75° C., about 60° C., about 65° C., about 70° C., etc., but is not limited thereto.

In an embodiment, the first unpaired strand and the second unpaired strand of the Y-form adaptor are the annealing regions of the primers. In an embodiment, the primers include a primer for amplification and a primer for nucleic acid sequencing. In an embodiment, the first unpaired strand of the Y-form adaptor includes a sequence identical to the primer used for amplification (for example, a first primer), and the second unpaired strand of the Y-form adaptor includes a sequence that is complementary to another primer used for amplification (for example, a second primer).

In an embodiment, the temperature range at which the first unpaired strand and the second unpaired strand of the Y-form adaptor are annealed to the primers may be about 20° C. to 72° C., such as about 25° C. to 70° C., about 30° C. to 65° C., about 35° C. to 60° C., about 40° C. to 55° C., about 52° C. to 70° C., about 55° C. to 68° C., about 45° C., about 58° C., about 60° C., about 62° C., about 65° C., etc., but is not limited thereto.

In an embodiment, the hairpin adaptor may be partially self-hybridized and form a hairpin. In an embodiment, the hairpin adaptor includes a paired double-stranded part (stem region) and an unpaired single-stranded part (loop region), wherein the double-stranded part may be linked to a double-stranded nucleic acid molecule with the target nucleotide sequence, and the unpaired single-stranded part has a loop structure.

In an embodiment, the length of the double-stranded part of the hairpin adaptor may be about 10 bp to 30 bp, such as about 12 bp to 28 bp, about 15 bp to 25 bp, about 18 bp, about 20 bp, etc., but is not limited thereto. Excessive length of the double-stranded part of the hairpin adaptor inhibits the PCR amplicon produced by a subsequent PCR reaction. In an embodiment, the length of the single-stranded part of the hairpin adaptor may be about 5 bp to 50 bp, such as about 10 bp to 45 bp, about 15 bp to 40 bp, about 20 bp to 35 bp, about 25 bp, about 30 bp, etc., but is not limited thereto. In an embodiment, the melting temperature of the hairpin adaptor may be about 30° C. to 90° C., such as about 35° C. to 85° C., about 40° C. to 80° C., about 45° C. to 75° C., about 35° C. to 65° C., about 40° C. to 60° C., about 45° C., about 50° C., about 55° C., about 68° C., about 72° C., about 85° C., etc., but is not limited thereto.

In an embodiment, the single-stranded part of the hairpin adaptor is the primer annealing region. In an embodiment, the primer includes a primer for amplification and a primer for nucleic acid sequencing. In an embodiment, the single-stranded part of the hairpin adaptor includes the same or complementary sequence as a primer pair (for example, a first primer and a second primer) used for amplification.

In an embodiment, the temperature range at which the single-stranded part of the hairpin adaptor and the primers are annealed may be about 20° C. to 72° C., such as about 25° C. to 70° C., about 30° C. to 65° C., about 35° C. to 60° C., about 40° C. to 55° C., about 52° C. to 70° C., about 55° C. to 68° C., about 26° C., about 37° C., about 46° C., about 58° C., about 60° C., about 62° C., about 65° C. etc., but is not limited thereto.

In an embodiment, the single-stranded part of the hairpin adaptor includes at least one uracil (U) base. In an embodiment, digestion may be performed at the position of the uracil (U) base in the single-stranded part of the hairpin adaptor by a uracil-specific digestion enzyme to form two separate strands (such as a first strand and a second strand), wherein the first strand and the second strand form a Y-shape. In an embodiment, the single-stranded part of the hairpin adaptor including the U base may be digested by a uracil-specific excision reagent (USER) enzyme (available from New England Biolabs; NEB) to create a single nucleotide gap at the uracil position. The USER enzyme is a mixture of uracil-DNA glycosylase (UDG) and DNA glycosylase-lyase endonuclease VIII (endoVIII). UDG catalyzes the removal of the uracil base to form an abasic site (AP site) (pyrimidine dione) while keeping the phosphodiester backbone intact. The lyase activity of endonuclease VIII destroyed the 3'- and 5'-phosphodiester backbones of the abasic site, thereby releasing abasic deoxyribose. In the above embodiment, uracil-DNA glycosylase and DNA glycosylase-lyase endonuclease VIII are mixed first (such as the USER enzyme), and then the single-stranded part of the hairpin adaptor including the U base is digested, but the disclosure is not limited thereto. In another embodiment, the single-stranded part including the U base of the hairpin adaptor may treat uracil-DNA glycosylase first, and then treat DNA glycosylase-lyase endonuclease VIII. In an embodiment, the first strand includes a sequence identical to a primer used for amplification (for example, a first primer), and the second strand includes a sequence complementary to another primer (for example, a second primer) used for amplification.

In an embodiment, the length of the primers is at least about 10 nucleotides, but not more than about 200 nucleotides.

In the present embodiment, the primers are designed to be specifically annealing to a known nucleotide sequence in a nucleic acid template. In an embodiment, the primers include sequences substantially complementary to the nucleic acid template, so the primers may be specifically annealing to the nucleic acid template. In an embodiment, the sequences in the primers hybridized with the nucleic acid template are located at the 3'-end of the primer sequences. The primers and the complements thereof may be annealed to form a double-stranded polynucleotide.

In the present embodiment, the first primer includes a first sequence that may be specifically annealing to the first adaptor near the forward strand, and the second primer includes a second sequence that may be specifically annealing to the first adaptor near the reverse strand.

In an embodiment, the first adaptor is a hairpin adaptor, wherein the first primer may be specifically annealing to the region of the single-stranded part near the forward strand, and the second primer may be specifically annealing to the region of the single-stranded part near the reverse strand. More specifically, the region of the single-stranded part near the forward strand includes a sequence identical to the first sequence, and the region of the single-stranded part near the reverse strand includes a sequence complementary to the second sequence.

In an embodiment, the first adaptor is a Y-form adaptor, wherein the first primer may be specifically annealing to the first unpaired strand near the forward strand, and the second primer may be specifically annealing to the second unpaired strand near the reverse strand. More specifically, the first unpaired strand near the forward strand includes a sequence identical to the first sequence, and the second unpaired strand near the reverse strand includes a sequence complementary to the second sequence.

In an embodiment, the first adaptor includes a nucleic acid marker or a molecular barcode. In an embodiment, the single-stranded part of the first adaptor includes a nucleic acid marker or a molecular barcode. In an embodiment, the double-stranded part of the first adaptor includes a nucleic acid marker or a molecular barcode. A nucleic acid marker or a molecular barcode may be used to align sequencing reads of amplicons derived from the same nucleic acid template, thereby allowing correction of errors caused by PCR amplification cycles. In other words, a nucleic acid marker or a molecular barcode may be used to mark the same initial nucleic acid template, so the error rate of analysis may be reduced. In an embodiment, the molecular barcode is single-stranded. In an embodiment, the first strand of the Y-form first adaptor includes a molecular barcode at the 3'-end of the unpaired part. In an embodiment, the molecular barcode is double-stranded.

In the present embodiment, the second adaptor is a hairpin adaptor. In an embodiment, the first adaptor is a hairpin adaptor, and the second adaptor is a hairpin adaptor different from the first adaptor. In an embodiment, the second adaptor is substantially not complementary with or substantially different from the first primer and the second primer.

In an embodiment, the linking of the adaptors and a double-stranded nucleic acid molecule with the target nucleotide sequence may be accomplished by any method known in the art, for example, blunt-end linking or sticky-end linking.

In an embodiment, the first adaptor may be linked to one end of a double-stranded nucleic acid molecule with the target nucleotide sequence first, and then the second adaptor is linked to the other end of the double-stranded nucleic acid molecule with the target nucleotide sequence. In another embodiment, the second adaptor may be linked to one end of the double-stranded nucleic acid molecule with the target nucleotide sequence first, and then the first adaptor is linked to the other end of the double-stranded nucleic acid molecule with the target nucleotide sequence.

In an embodiment, the denaturation reaction is achieved by heating the nucleic acid template at a sufficiently high temperature. In an embodiment, the sufficiently high temperature is about 90° C. to 100° C., such as about 92° C., about 95° C., about 98° C., etc., but is not limited thereto. In an embodiment, the denaturation reaction of the nucleic acid template is, for example, performing a bisulfite treatment on the nucleic acid template. The bisulfite treatment may convert the cytosine (C) in the nucleic acid template into uracil (U), thereby changing the base pairing specificity. Specifically, the original cytosine (C) is paired with guanine (G) (C-G pairing). However, after bisulfite conversion, cytosine is converted to uracil (U), and uracil (U) and guanine (G) form a non-complementary base pairing (G-U pairing), so the nucleic acid template may be denatured into single strands. In an embodiment, the conversion rate of the bisulfite treatment is 60% or more. In an embodiment, the conversion rate of the bisulfite treatment may be about 70% to 100%, such as about 75%, 80%, 85%, 90%, 95%, etc., but is not limited thereto.

In an embodiment, the first adaptor is a hairpin adaptor, and before step (c), the nucleic acid template may be further amplified. In an embodiment, the nucleic acid template is amplified using rolling circle amplification (RCA) to synthesize complementary replicas with a large number of nucleic acid template sequences. Specifically, both the first adaptor and the second adaptor are hairpin adaptors. Therefore, the denatured nucleic acid template is a circular nucleic acid molecule (including a first adaptor sequence, a forward strand sequence, a second adaptor sequence, and a reverse strand sequence), and this circular nucleic acid molecule may be used as a template for RCA. In an embodiment, RCA may synthesize a nucleic acid molecule product of at least two nucleic acid template sequences.

In an embodiment, RCA is performed using at least one complementary primer. In an embodiment, the complementary primer is complementary to the target nucleotide sequence of the nucleic acid template. In an embodiment, the complementary primer is complementary to at least one of the first adaptor and the second adaptor of the nucleic acid template. In an embodiment, the RCA is multiple primer RCA. In the present embodiment, the RCA is performed using a method known in the art, which is not repeated herein.

In the present embodiment, under conditions sufficient for PCR amplification of the target nucleotide sequence, one or a plurality of polymerase chain reaction (PCR) amplification cycles are performed on the nucleic acid template or complementary replicas using primers used for amplification (i.e., the first primer and the second primer). PCR amplification cycles may exponentially increase the abundance of the target nucleotide sequence. In an embodiment, the method includes at least 2 or more PCR amplification cycles, such as at least about any one of 5, 10, 15, 20, 25, 30, or more repeated PCR amplification cycles. In an embodiment, the method may include about 30 to 50 PCR amplification cycles. Each PCR amplification cycle includes the following steps: 1) strand separation (such as thermal denaturation); 2) annealing of the first primer and the second primer to the nucleic acid template; and 3) DNA polymerase extension of the annealed primers. Those skilled in the art may design the conditions and time required for each of these steps.

In an embodiment, PCR amplification cycles are performed under the following exemplary conditions. 1) Sustain at 95° C. for 5 minutes; 2) then perform 10 to 25 cycles, including: denaturation at 95° C. for 30 seconds, then annealing at 56° C. and extension at 72° C. for 1 minute; 3) maintain the completed reaction at 4° C. However, the disclosure is not limited thereto, and other appropriate reaction conditions may also be used.

In an embodiment, after the PCR amplification cycles are performed, the PCR amplicon may be further purified. In an embodiment, the PCR amplicon may be further analyzed, such as nucleic acid sequencing, DNA microarray analysis, etc., but the disclosure is not limited thereto. In an embodiment, the PCR amplicon of the target nucleotide sequence may be used for next-generation sequencing (NGS).

In an embodiment, the first adaptor includes a sequence the same as or complementary to a first sequencing primer used for nucleic acid sequencing and a sequence the same as or complementary to a second sequencing primer used for nucleic acid sequencing.

In an embodiment, the first unpaired strand of the Y-form first adaptor includes a sequence the same as or complementary to the first sequencing primer used for nucleic acid sequencing, and the second unpaired strand includes a sequence the same as or complementary to the second sequencing primer used for nucleic acid sequencing.

In an embodiment, the single-stranded part of the hairpin first adaptor includes a sequence the same as or complementary to the first sequencing primer used for sequencing and a sequence the same as or complementary to the second sequencing primer used for sequencing.

In an embodiment, the first strand formed by the digestion with uracil-DNA glycosylase and DNA glycosylase-lyase endonuclease VIII (such as the USER enzyme) includes a sequence the same as or complementary to the first sequencing primer used for sequencing, and the second strand includes a sequence the same as or complementary to the second sequencing primer used for sequencing.

In an embodiment, the first adaptor is a hairpin adaptor, wherein the first sequencing primer may be specifically annealing to the region of the single-stranded part near the forward strand, and the second sequencing primer may be specifically annealing to the region of the single-stranded part near the reverse strand. In an embodiment, the region of the single-stranded part near the forward strand includes the same or complementary sequence as the first sequencing primer, and the region of the single-stranded part near the reverse strand includes the same or complementary sequence as the second sequencing primer.

In an embodiment, the first adaptor is a Y-form adaptor, wherein the first sequencing primer is specifically annealing to the first unpaired strand near the forward strand, and the second sequencing primer is specifically annealing to the second unpaired strand near the reverse strand.

In an embodiment, the first adaptor is a hairpin adaptor, wherein the region of the single-stranded part near the forward strand and/or the first primer may include a sequence the same as or complementary to the sequence of the first sequencing primer, and the region of the single-stranded part near the reverse strand and/or the second primer may include a sequence the same as or complementary to the sequence of the second sequencing primer.

In an embodiment, the first adaptor is a Y-form adaptor, wherein the first unpaired strand and/or the first primer may include a sequence the same as or complementary to the sequence of the first sequencing primer, and the second unpaired strand and/or the second primer may include a sequence the same as or complementary to the sequence of the second sequencing primer.

In an embodiment, the first primer includes a sequence the same as or complementary to the first sequencing primer, and the second primer includes a sequence the same as or complementary to the second sequencing primer. In an embodiment, the 5'-end of the first primer includes a sequence the same as or complementary to the first sequencing primer, and the 5'-end of the second primer includes a sequence the same as or complementary to the second sequencing primer.

In an embodiment, the sequencing direction of the first sequencing primer is opposite to the sequencing direction of the second sequencing primer. In an embodiment, the first sequencing primer and the second sequencing primer are used for NGS. In an embodiment, the first sequencing primer and the second sequencing primer include primer sequences based on NGS techniques.

In an embodiment, the second adaptor is substantially not complementary to or substantially different from the first sequencing primer and the second sequencing primer. In an embodiment, the second adaptor is substantially not complementary to or substantially different from the first primer, the second primer, the first sequencing primer, and the second sequencing primer.

In the present embodiment, the two complementary strands of DNA (i.e., the forward strand and the reverse strand) of the target nucleotide sequence are held together by the hairpin second adaptor and used as a nucleic acid template, and PCR amplification cycles are performed on the nucleic acid template using primers located on the first adaptor. Therefore, any strand of the resulting PCR amplicon has the forward target nucleotide sequence, the second adaptor sequence, the reverse target nucleotide sequence, and parts of the first adaptor sequence located at the two ends, wherein the second adaptor sequence links the forward target nucleotide sequence and the reverse target nucleotide sequence together. Since any strand of the PCR amplicon includes the forward target nucleotide sequence and the reverse target nucleotide sequence, during subsequent nucleic acid sequencing analysis, the sequences of two complementary strands of DNA regions may be obtained by sequencing from either end, and the sequences of the resulting two complementary strands of DNA regions may be aligned with each other, thereby improving the accuracy of the original sequence. In addition, in the present embodiment, two complementary strands of DNA are held together for sequencing and analysis, so the cost of sequencing may be reduced. Moreover, in the disclosure, specific sequences for nucleic acid sequencing are introduced during the enrichment of the target nucleotide sequence (for example, sequence design on the first adaptor or the first primer and the second primer). Therefore, the sequencing direction obtained by sequencing may be distinguished by the above design.

The disclosure further provides a method of determining a target nucleotide sequence including the following steps. First, the PCR amplicon of the target nucleotide sequence obtained by the method of amplifying a target nucleotide sequence is provided. Next, nucleic acid sequencing is performed on the PCR amplicon of the target nucleotide sequence to obtain sequence information of the target nucleotide sequence.

In an embodiment, the nucleic acid sequencing is NGS.

In an embodiment, the method further includes preparing a sequencing DNA library using the PCR amplicon of the target nucleotide sequence before nucleic acid sequencing. In an embodiment, the method includes quantifying PCR amplicons of target nucleotide sequences from a plurality of samples, and merging the PCR amplicons of the target nucleotide sequences together as a single sequencing DNA library. In an embodiment, the PCR amplicon of the target nucleotide sequence is linked to the adaptors, thereby constructing a sequencing DNA library for the sequencing step. In an embodiment, the PCR amplicon may be further fragmented.

The method of the disclosure may be used in various applications, such as clinical diagnosis or as a tool for genetic engineering, but the disclosure is not limited thereto. In an embodiment, the method may be used to determine the target nucleotide sequence of a locus of interest, and to detect a sequence variant in the target nucleotide sequence. In an embodiment, the sequence variant is a sequence variant associated with a disease (such as a genetic disorder or cancer).

In order to thoroughly understand the disclosure, the steps of amplifying the target nucleotide sequence are described in detail below. However, well-known compositions or process steps are not described in the details to avoid limiting the disclosure. Embodiments of the disclosure are described in detail as follows, but the disclosure is not limited thereto. The disclosure may also be widely implemented in other embodiments, and the scope of the disclosure is not limited, which shall be based on the subsequent claims.

FIG. 1 is a flowchart of a method of amplifying a target nucleotide sequence according to the first embodiment of the disclosure. The method of amplifying a target nucleotide sequence of the first embodiment includes the following steps.

First, step a) is performed to link a Y-form first adaptor 101 and a hairpin second adaptor 102 to two ends of a double-stranded nucleic acid molecule 100 with a target nucleotide sequence respectively to form a nucleic acid template 10, wherein the target nucleotide sequence includes a forward strand and a reverse strand. The Y-form first adaptor 101 has an unpaired Y5 strand 105 and Y3 strand 103. In particular, the Y5 strand 105 and the Y3 strand 103 may be directional. For example, the Y5 strand 105 may be the 5'-end of the Y-form first adaptor, and the Y3 strand 103 may be the 3'-end of the Y-form first adaptor, but are not limited thereto. In the present embodiment, the nucleic acid template 10 is a hairpin construct.

Next, step b) is performed to perform a denaturation reaction on the nucleic acid template 10 to dissociate the double-stranded nucleic acid template 10 into single strands. In the present embodiment, the denaturation reaction of the nucleic acid template 10 is, for example, performing a bisulfate treatment on the nucleic acid template 10.

Then, step c) is performed to perform multiple PCR amplification cycles using a first primer 106 located on the Y5 strand 105 of the first adaptor 101 and a second primer 104 located on the Y3 strand 103 of the first adaptor 101 to obtain a PCR amplicon 20 of the target nucleotide sequence. In the present embodiment, the first primer 106 includes a first sequence specifically annealing to the Y5 strand 105 near the forward strand, and the second primer 104 includes a second sequence specifically annealing to the Y3 strand 103 near the reverse strand. In the present embodiment, the PCR amplicon 20 includes a forward target nucleotide sequence 100a and a reverse target nucleotide sequence 100b.

In the present embodiment, the first primer 106 has a sequence the same as or complementary to the first sequencing primer running a first sequencing direction 112, and the second primer 104 has a sequence the same as or complementary to the second sequencing primer running a second sequencing direction 114.

In the present embodiment, nucleic acid sequencing may further be performed on the PCR amplicon 20. In the present embodiment, the nucleic acid sequencing is, for example, NGS.

In the present embodiment, since any strand of the PCR amplicon 20 includes the forward target nucleotide sequence and the reverse target nucleotide sequence, when nucleic acid sequencing is performed, sequencing from either end may produce the forward target nucleotide sequence and the reverse target nucleotide sequence. In addition, by aligning the resulting forward target nucleotide sequence and the reverse target nucleotide sequence with each other, the accuracy of restoring the original sequence may be improved. In addition, in the present embodiment, two complementary strands of DNA are held together for sequencing and analysis, so the cost of sequencing may be reduced.

Figure 2:
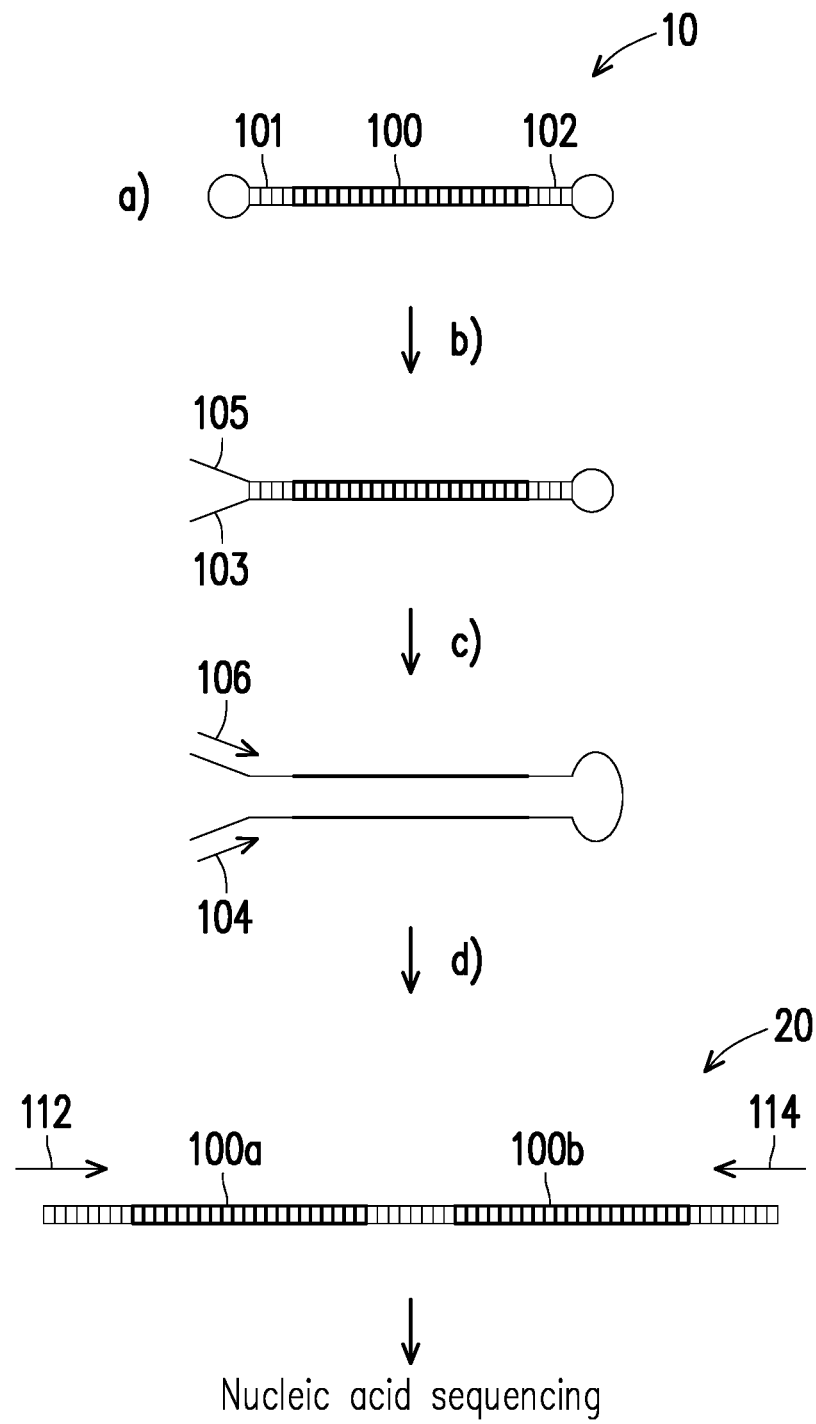
FIG. 2 is a flowchart of a method of amplifying a target nucleotide sequence according to the second embodiment of the disclosure.

FIG. 2 is a flowchart of a method of amplifying a target nucleotide sequence according to the second embodiment of the disclosure. The embodiment below uses some of the reference numerals and contents of the above embodiments. In particular, the same reference numerals are used to represent the same components, and description of the same technical content is omitted. The method of amplifying a target nucleotide sequence of the second embodiment includes the following steps.

First, step a) is performed to link the hairpin first adaptor 101 and the hairpin second adaptor 102 to two ends of the double-stranded nucleic acid molecule 100 with a target nucleotide sequence respectively to form the nucleic acid template 10, wherein the target nucleotide sequence includes a forward strand and a reverse strand. In the present embodiment, the nucleic acid template 10 is a circular construct. In the present embodiment, the single-stranded part with a loop structure of the first adaptor 101 includes one U base.

Next, step b) is performed to digest at the position of the U base of the single-stranded part with a loop structure by uracil-DNA glycosylase and DNA glycosylase-lyase endonuclease VIII to form the two separate Y5 strand 105 and Y3 strand 103. In this step, the nucleic acid template 10 is digested to form a hairpin construct.

Next, step c) is performed to perform a denaturation reaction on the nucleic acid template 10 to dissociate the double-stranded nucleic acid template 10 into single strands. In the present embodiment, the denaturation reaction of the nucleic acid template 10 is, for example, performing a bisulfate treatment on the nucleic acid template 10.

Then, step d) is performed to perform multiple PCR amplification cycles using the first primer 106 located on the Y5 strand 105 of the first adaptor 101 and the second primer 104 located on the Y3 strand 103 of the first adaptor 101 to obtain a PCR amplicon 20 of the target nucleotide sequence. In the present embodiment, the first primer 106 has a sequence the same as or complementary to the first sequencing primer running the first sequencing direction 112, and the second primer 104 has a sequence the same as or complementary to the second sequencing primer running the second sequencing direction 114. In the present embodiment, the PCR amplicon 20 includes the forward target nucleotide sequence 100a and the reverse target nucleotide sequence 100b.

In the present embodiment, nucleic acid sequencing may be further performed on the PCR amplicon 20.

Figure 3:
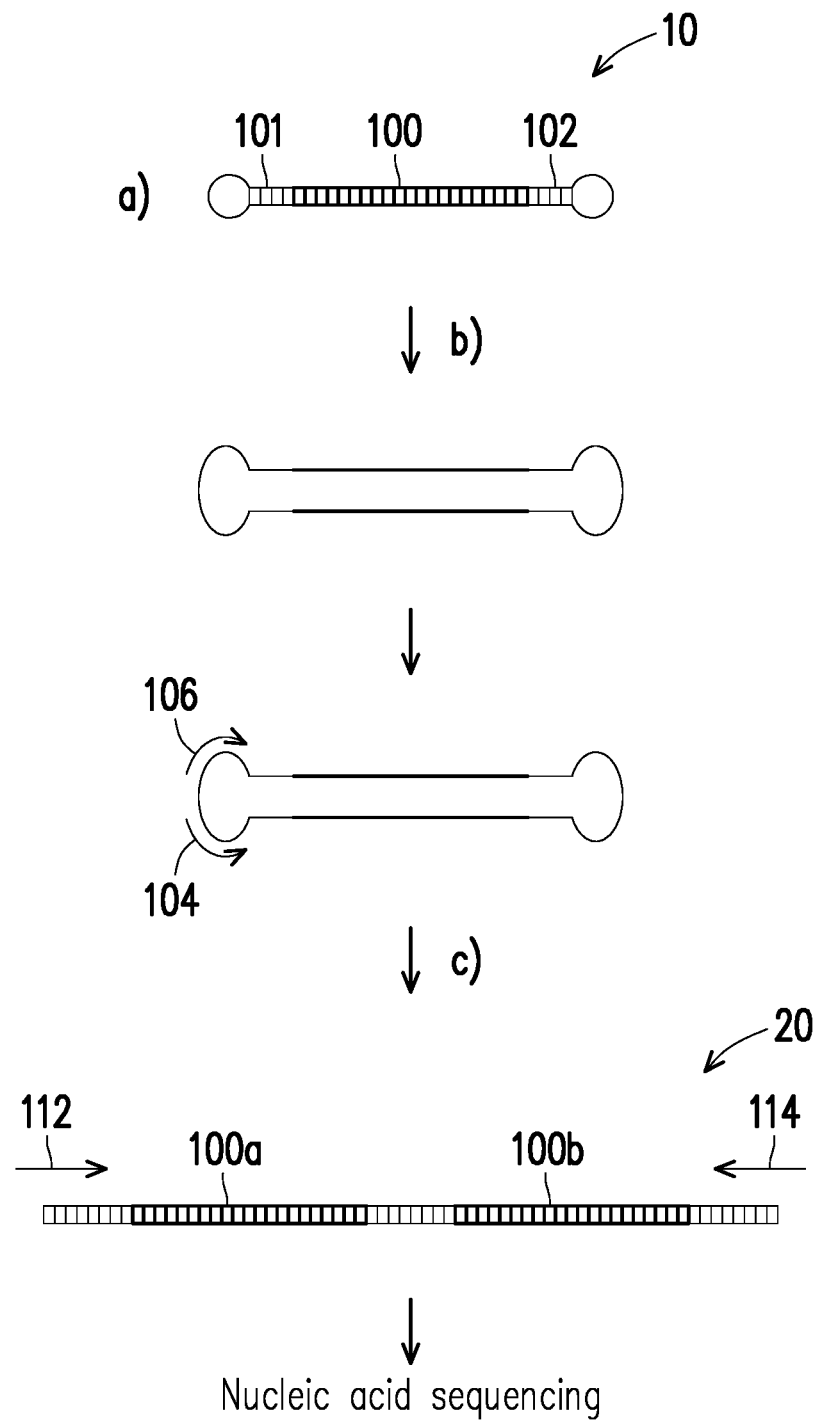
FIG. 3 is a flowchart of a method of amplifying a target nucleotide sequence according to the third embodiment of the disclosure.

FIG. 3 is a flowchart of a method of amplifying a target nucleotide sequence according to the third embodiment of the disclosure. The embodiment below uses some of the reference numerals and contents of the above embodiments. In particular, the same reference numerals are used to represent the same components, and description of the same technical content is omitted. The method of amplifying a target nucleotide sequence of the third embodiment includes the following steps.

First, step a) is performed to link the hairpin first adaptor 101 and the hairpin second adaptor 102 to two ends of the double-stranded nucleic acid molecule 100 with a target nucleotide sequence respectively to form the nucleic acid template 10, wherein the target nucleotide sequence includes a forward strand and a reverse strand. The first adaptor 101 includes a paired double-stranded part and an unpaired single-stranded part. In the present embodiment, the nucleic acid template 10 is a circular construct.

Next, step b) is performed to perform a denaturation reaction on the nucleic acid template 10 to dissociate the double-stranded nucleic acid template 10 into single-stranded circular molecules. In the present embodiment, the denaturation reaction of the nucleic acid template 10 is, for example, performing a bisulfate treatment on the nucleic acid template 10.

Then, step c) is performed to perform multiple PCR amplification cycles using the first primer 106 located on the region near the forward strand of the first adaptor 101 and the second primer 104 located on the region near the reverse strand of the first adaptor 101 to obtain the PCR amplicon 20 of the target nucleotide sequence. In the present embodiment, the first primer 106 includes a first sequence specifically annealing to the single-stranded part, and the second primer 104 includes a second sequence specifically annealing to the single-stranded part. In the present embodiment, the first primer 106 has a sequence the same as or complementary to the first sequencing primer running the first sequencing direction 112, and the second primer 104 has a sequence the same as or complementary to the second sequencing primer running the second sequencing direction 114. In the present embodiment, the PCR amplicon 20 includes the forward target nucleotide sequence 100a and the reverse target nucleotide sequence 100b.

In the present embodiment, nucleic acid sequencing may be further performed on the PCR amplicon 20.

Figure 4:
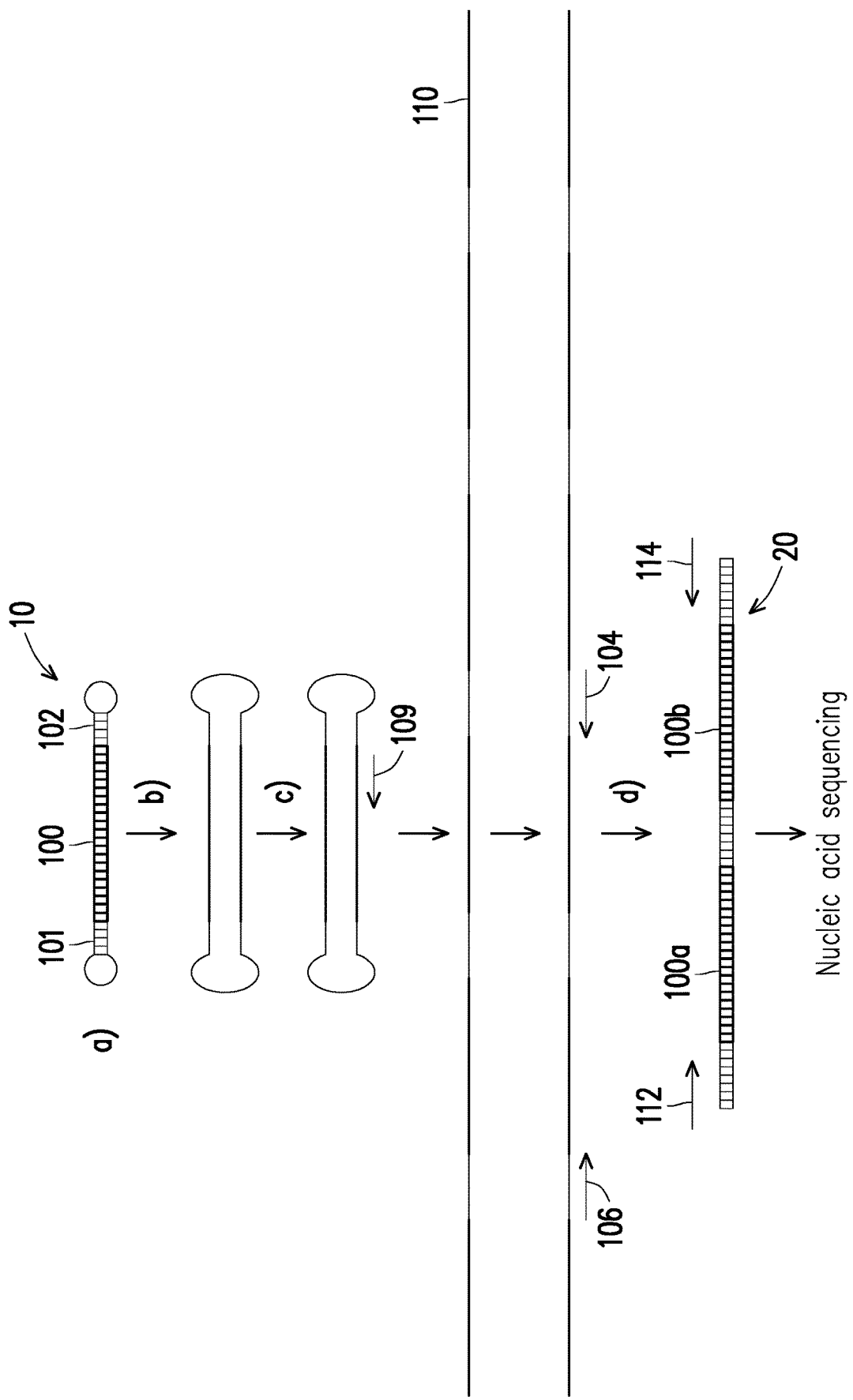
FIG. 4 is a flowchart of a method of amplifying a target nucleotide sequence according to the fourth embodiment of the disclosure.

FIG. 4 is a flowchart of a method of amplifying a target nucleotide sequence according to the fourth embodiment of the disclosure. The embodiment below uses some of the reference numerals and contents of the above embodiments. In particular, the same reference numerals are used to represent the same components, and description of the same technical content is omitted. The method of amplifying a target nucleotide sequence of the fourth embodiment includes the following steps.

First, step a) is performed to link the hairpin first adaptor 101 and the hairpin second adaptor 102 to two ends of the double-stranded nucleic acid molecule 100 with a target nucleotide sequence respectively to form the nucleic acid template 10, wherein the target nucleotide sequence includes a forward strand and a reverse strand. In the present embodiment, the nucleic acid template 10 is a circular construct.

Next, step b) is performed to perform a denaturation reaction on the nucleic acid template 10 to dissociate the double-stranded nucleic acid template 10 into single-stranded circular molecules. In the present embodiment, the denaturation reaction of the nucleic acid template 10 is, for example, performing a bisulfate treatment on the nucleic acid template 10.

Then, step c) is performed to perform RCA on the single-stranded circular molecules (the nucleic acid template 10) using a complementary primer 109 located on the target nucleotide sequence to obtain a complementary replica 110 with a large number of nucleic acid template sequences. In the present embodiment, the complementary primer 109 is located on the reverse strand, but the disclosure is not limited thereto. In another embodiment, the complementary primer 109 is located on the forward strand. In the present embodiment, the complementary reverse strand sequence, the complementary first adaptor sequence, the complementary forward strand sequence, and the complementary second adaptor sequence are repeated in the complementary replica 110 in this order.

Then, step d) is performed to perform multiple PCR amplification cycles using the first primer 106 located on the region near the complementary forward strand of the complementary first adaptor sequence and the second primer 104 located on the region near the complementary reverse strand of the complementary first adaptor sequence to obtain the PCR amplicon 20 of the target nucleotide sequence. In the present embodiment, the first primer 106 includes a first sequence that may be specifically annealing to the single-stranded part, and the second primer 104 includes a second sequence that may be specifically annealing to the single-stranded part. In the present embodiment, the first primer 106 has a sequence the same as or complementary to the first sequencing primer running the first sequencing direction 112, and the second primer 104 has a sequence the same as or complementary to the second sequencing primer running the second sequencing direction 114. In the present embodiment, the PCR amplicon 20 includes the forward target nucleotide sequence 100a and the reverse target nucleotide sequence 100b.

In the present embodiment, nucleic acid sequencing may be further performed on the PCR amplicon 20.

Figure 5:
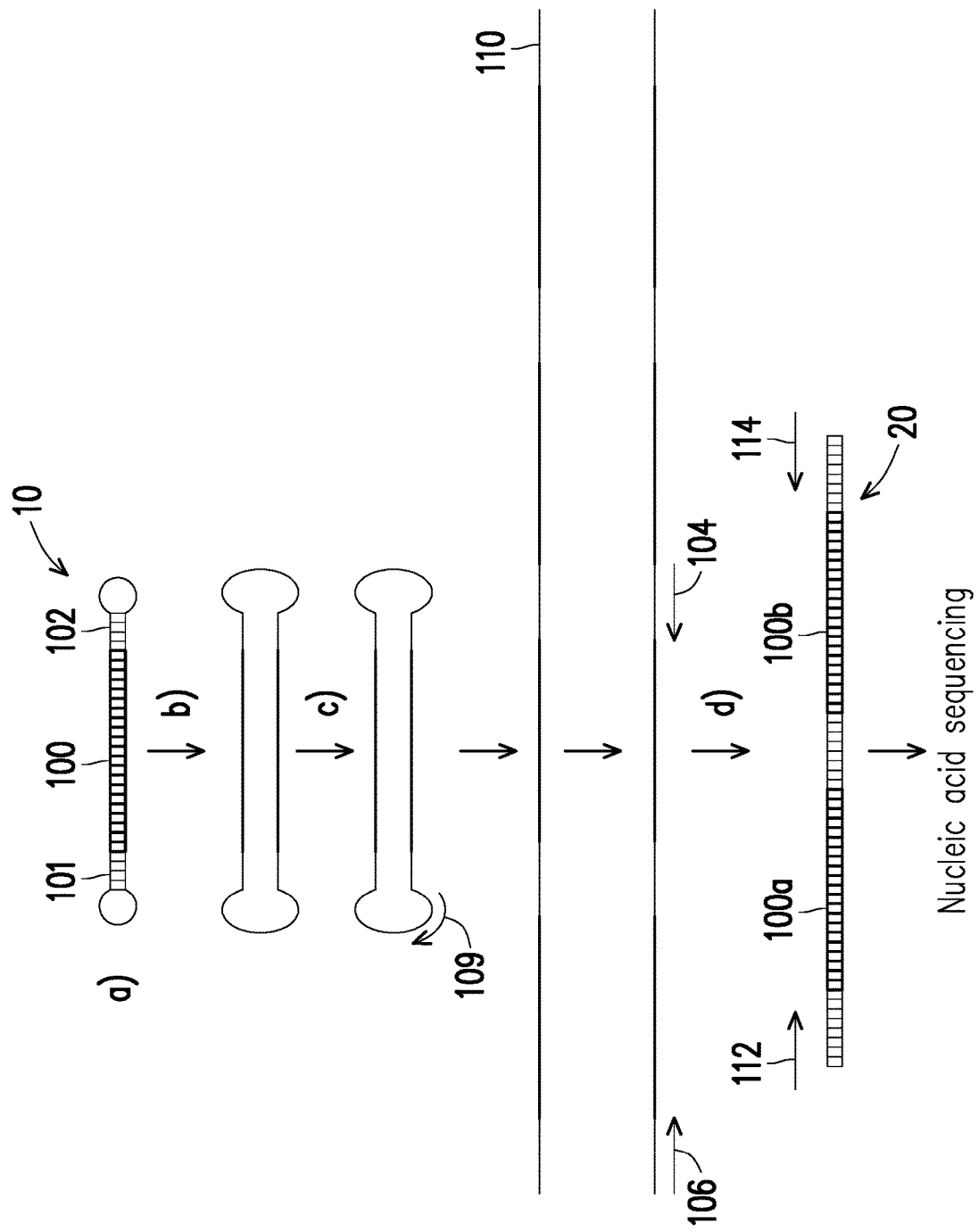
FIG. 5 is a flowchart of a method of amplifying a target nucleotide sequence according to the fifth embodiment of the disclosure.

FIG. 5 is a flowchart of a method of amplifying a target nucleotide sequence according to the fourth embodiment of the disclosure. The embodiment below uses some of the reference numerals and contents of the above embodiments. In particular, the same reference numerals are used to represent the same components, and description of the same technical content is omitted. The method of amplifying a target nucleotide sequence of the fifth embodiment includes the following steps.

First, step a) is performed to link the hairpin first adaptor 101 and the hairpin second adaptor 102 to two ends of the double-stranded nucleic acid molecule 100 with a target nucleotide sequence respectively to form the nucleic acid template 10, wherein the target nucleotide sequence includes a forward strand and a reverse strand. In the present embodiment, the nucleic acid template 10 is a circular construct.

Next, step b) is performed to perform a denaturation reaction on the nucleic acid template 10 to dissociate the double-stranded nucleic acid template 10 into single-stranded circular molecules. In the present embodiment, the denaturation reaction of the nucleic acid template 10 is, for example, performing a bisulfate treatment on the nucleic acid template 10.

Then, step c) is performed to perform RCA on the single-stranded circular molecules (the nucleic acid template 10) using the complementary primer 109 located on the first adaptor 101 to obtain the complementary replica 110 with a large number of nucleic acid template sequences. In the present embodiment, the complementary primer 109 is located on the first adaptor 101, but the disclosure is not limited thereto. In another embodiment, the complementary primer 109 is located on the second adaptor 102. In the present embodiment, the complementary first adaptor sequence, the complementary forward strand sequence, the complementary second adaptor sequence, and the complementary reverse strand sequence are repeated in the complementary replica 110 in this order.

Then, step d) is performed to perform multiple PCR amplification cycles using the first primer 106 located on the region near the complementary forward strand of the complementary first adaptor sequence and the second primer 104 located on the region near the complementary reverse strand of the complementary first adaptor sequence to obtain the PCR amplicon 20 of the target nucleotide sequence. In the present embodiment, the first primer 106 includes a first sequence that may be specifically annealing to the single-stranded part, and the second primer 104 includes a second sequence that may be specifically annealing to the single-stranded part. In the present embodiment, the first primer 106 has a sequence the same as or complementary to the first sequencing primer running the first sequencing direction 112, and the second primer 104 has a sequence the same as or complementary to the second sequencing primer running the second sequencing direction 114. In the present embodiment, the PCR amplicon 20 includes the forward target nucleotide sequence 100a and the reverse target nucleotide sequence 100b.

In the present embodiment, nucleic acid sequencing may be further performed on the PCR amplicon 20.

Hereinafter, experimental examples of the disclosure are provided to more specifically validate the disclosure. However, without departing from the spirit of the disclosure, the materials and usage methods . . . etc. in the following experimental examples may be suitably modified. Therefore, the scope of the disclosure should not be construed to the following experimental examples.

Experimental Example 1: Construction of Hairpin Construct

Figure 6:
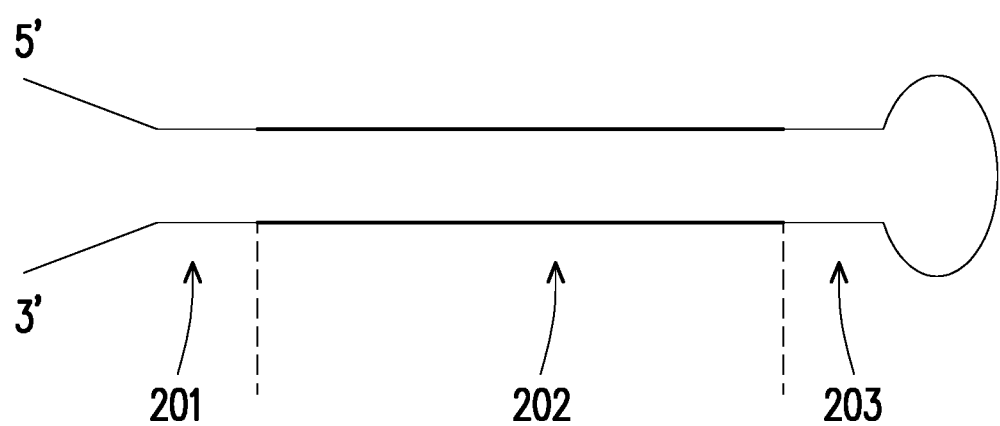
FIG. 6 shows an exemplary structure of a hairpin construct.

FIG. 6 shows an exemplary structure of a hairpin construct. In the present embodiment, the hairpin construct includes three parts: a Y-form construct 201, a target double-stranded nucleic acid molecule 202, and a stem-loop construct 203, wherein the Y-form construct 201 is derived from a Y-form adaptor, the stem-loop construct 203 is derived from a hairpin adaptor, and the target double-stranded nucleic acid molecule 203 has the target nucleotide sequence. The three parts of this hairpin construct are detailed below.

[Design of Y-Form Construct]

In the present embodiment, the length of the stem part (that is, the paired double-stranded DNA part) of the Y-form construct 201 is 12 bp, including two 6-base restriction sites (SacI and EcoRI), namely gagctcgaattc (SEQ ID NO: 1). The unpaired part of the Y-form construct 201 includes the Y5 strand (unpaired strand at the 5'-end) and the Y3 strand (unpaired strand at the 3'-end), each of which is 25 bp in length. In the present embodiment, the sequences of the Y5 strand and Y3 strand are specific sequences for the human genome, and are regional sequences suitable for PCR with PCR primers.

[Design of Stem-Loop Construct]

In the present embodiment, the length of the stem part (that is, the paired double-stranded DNA part) of the stem-loop construct 203 is 12 bp, including two 6-base restriction sites (BamHI and XbaI), namely ggatcctctaga (SEQ ID NO: 2). The length of the loop part of the stem-loop construct 203 is 25 bp. In the present embodiment, the sequence of the loop part of the stem-loop construct 203 is a specific sequence for the human genome, and is a regional sequence suitable for PCR with PCR primers.

[Design of Target Double-Stranded Nucleic Acid Molecule]

In the present embodiment, the length of the target double-stranded nucleic acid molecule 202 is 100 bp, with the nucleotide sequence of SEQ ID NO:3.

[Construction of Hairpin Construct]

The following 2 oligonucleotides (Oligo-186 and Oligo-137) as shown in Table 1 are provided.

TABLE 1

| Name | Sequence | SEQ ID NO |
|---|---|---|
| Oligo-186 | AGATGAGAAAGAAAGAGTAGG/iMe-dC/A/iMe-dC/ Agagctcgaattc AAGGTACT/iMe-dC/GTGCTGTATCTA CAACTGAGGGAGCTGGGTGCTGACACCCCAAAA GGC/iMe-dC/GCACTTTTCCCCTTAAGAGAGTAAA CTTGTTT/iMe-dC/GAAGGCAGAGgatcctctagagtctctcg cgccccttgcctcatctctagaggatcc | SEQ ID NO: 4 |

TABLE 1-continued

| Name | Sequence | SEQ ID NO |
|---|---|---|
| Oligo-137 | TCTGCCTTCGAAACAAGTTTACTCTCTTAAGGGG AAAAGTGCGGCCTTTTGGGGTGTCAGCACCCAGC TCCCTCAGTTGTAGATACAGCACGAGTACCTTgaat tcgagct/iMe-dC/TT/iMe-dC//iMe-dC/AAAATTGG/iMe-dC//iMe-dC/AAAGG/iMe-dC/TATAG | SEQ ID NO: 5 |

Oligo-186 includes the following regions in sequence: the Y5 strand, the stem part (forward) of the Y-form construct, the target double-stranded nucleic acid molecule (forward), the stem part (forward) of the stem-loop construct, the loop part of the Y-form construct, and the stem part (reverse) of the stem-loop construct. Oligo-137 includes the following regions in sequence: the target double-stranded nucleic acid molecule (reverse), the stem part (reverse) of the Y-form construct, and the Y3 strand. In the present embodiment, iMe-dC represents methylated cytosine. Oligo-186 and Oligo-137 were synthesized by Medclub Scientific Co. Ltd., Taiwan.

An annealing reaction was performed on Oligo-186 and Oligo-137. 10 μL of Oligo-137, 10 μL of Oligo-186, 3 μL of a 10× T4 ligase buffer (New England Biolabs; NEB), and 7 μL of double distilled water (ddH₂O) were mixed to obtain an annealing mixed solution with a total volume of 30 μL (see Table 2). The annealing mixed solution was denatured at 95° C. for 5 minutes. Then, the temperature was slowly lowered at room temperature (about 25° C.) to perform the annealing reaction.

TABLE 2

| Components of annealing mixed solution | Volume (μL) | Concentration (ng/μL) | DNA content (ng) |
|---|---|---|---|
| Oligo-137 | 10 | 4.2382 | 42.382 |
| Oligo-186 | 10 | 5.7574 | 57.574 |
| 10X T4 ligase buffer | 3 | 9.9956 | 99.956 |
| ddH₂O | 7 | — | — |
| Total volume | 30 | — | — |

The annealing mixed solution (30 μL) was added to 2 μL of a 10× T4 ligase buffer, 2.5 μL of T4 ligase (New England Biolabs; NEB), and 15.5 μL of ddH₂O to obtain a ligation mixed solution with a total volume of 50 μL (see Table 3). A ligation reaction was performed on the ligation mixed solution at room temperature (about 25° C.) for 30 minutes to form a hairpin construct as a nucleic acid template. At this point, the structure shown in step a) of FIG. 1 and FIG. 6 may be obtained.

TABLE 3

| Components of ligation mixed solution | Volume (μL) |
|---|---|
| Annealing mixed solution | 30 |
| 10X T4 ligase buffer | 2 |
| T4 ligase | 2.5 |
| ddH₂O | 15.5 |
| Total volume | 50 |

Experimental Example 2: Bisulfite Treatment of Hairpin Construct

In the present embodiment, the hairpin construct of Experimental example 1 was treated with bisulfite using the EpiTect Fast Bisulfite Kit (10) (QIAGEN Cat No./ID: 59802) of QIAGEN Taiwan Company Ltd. Specifically, 10 μL of the ligation mixed solution (including 19.9912 ng DNA), 30 μL of an RNase-free water, 85 μL of a bisulfite solution, and 15 μL of a DNA protect buffer were mixed to obtain a bisulfite conversion solution with a total volume of 140 μL (shown in Table 4).

TABLE 4

| Components of bisulfite conversion solution | Volume (μL) |
|---|---|
| Annealing mixed solution | 10 |
| RNase-free water | 30 |
| Bisulfite solution | 85 |
| DNA protect buffer | 15 |
| Total volume | 140 |

The bisulfite conversion solution was denatured at 95° C. for 5 minutes, and then a bisulfite conversion reaction was performed at 60° C. for 10 minutes. Then, the bisulfite conversion solution was denatured at 95° C. for 5 minutes, and then a bisulfite conversion reaction was performed at 60° C. for 10 minutes. Then, the reacted bisulfite conversion solution was placed at 20° C. for later use. At this point, the structure shown in step b) of FIG. 1 may be obtained.

Experimental Example 3: Simulation of Detecting the Methylation of Bisulfite-Converted Hairpin Construct

[PCR Reaction of Bisulfite-Converted Hairpin Construct]
In the present embodiment, a PCR reaction was performed on the bisulfite-converted hairpin construct (hereinafter referred to as BS DNA) using a primer F (with the nucleotide sequence of SEQ ID NO: 6) and a primer R (with the nucleotide sequence of SEQ ID NO: 7) to obtain the PCR amplicon of the target nucleotide sequence. The sequences of the primer F and the primer R are shown in Table 5. The length of the resulting PCR amplicon was 320 bp.

TABLE 5

| Name | Sequence | SEQ ID NO |
|---|---|---|
| Primer F | ATGAGAAAGAAAGAGTAGGCACAGA | SEQ ID NO: 6 |
| Primer R | TATAGCCTTTGGCCAATTTTGGAAG | SEQ ID NO: 7 |

The components of the PCR reaction solution are shown in Table 6 below.

TABLE 6

| Components of PCR reaction solution | Volume (μL) |
| --- | --- |
| BS DNA | 3 |
| KAPA PCR 2X reagent | 25 |
| Primer F (100 μM) | 0.25 |
| Primer R (100 μM) | 0.25 |
| ddH$_2$O | 21.5 |
| Total volume | 50 |

The PCR reaction was performed with the PCR reaction solution as follows: (1) 10 minutes at 95° C.; (2) perform the following 40 cycles [20 seconds at 95° C.; 30 seconds at 56° C.; 40 seconds at 72° C.]; (3) 7 minutes at 72° C.

[Computer Simulation of in Silico Bisulfite Conversion and Sequence Alignment Thereof]

In the present embodiment, the hairpin construct designed in Experimental example 1 starts to sequence the nucleotide sequence that may have SEQ ID NO: 8 from the Y5 strand. In Experimental example 2, the in silico BS DNA starts to sequence the nucleotide sequence that may have SEQ ID NO: 9 from the Y5 strand.

FIG. 7 shows the nucleotide sequence alignment of SEQ ID NO: 8 and SEQ ID NO: 9. As shown in FIG. 7, the designed hairpin construct (SEQ ID NO: 8) has 11 methylated cytosines (marked by ▲), wherein three are in the target nucleic acid molecule regions, and 8 are in the primer regions (Y5 strand and Y3 strand), and there are 71 sites at which the cytosines may be converted by bisulfite (that is, cytosines that are not originally methylated). The sequence (SEQ ID NO: 9) of the in silico BS DNA simulates the conversion of all unmethylated cytosine (C) in the sequence into uracil (U)/thymine (T).

[Analysis of BS-Conversion Rate]

Detection of methylation using bisulfate sequencing is in principle to convert all unmethylated cytosines (C) into uracil (U)/thymine (T), while methylated cytosines (C) remain unchanged, to distinguish the methylation of cytosines (C) in the sequence. Therefore, the conversion of all "cytosine (C) originally not methylated" into "uracil (U)/thymine (T)" is an important step.

The estimation method used in the present embodiment is to first mark the "positions of unmethylated C" in the sequencing results (sequences) obtained individually, and then calculate the ratio of the conversion (C→T or C→C) thereof. In the present embodiment, the sequences used for alignment are sorted in a "paired-end sequencing" manner. Specifically, forward sequencing and backward sequencing are performed on the PCR amplicon from the Y5 strand and the Y3 strand, and alignment is performed using the forward sequence and the reverse sequence; or the reverse sequence is converted into a reverse complementary sequence and then aligned with the forward sequence. In the present embodiment, the reverse complementary sequence (SEQ ID NO: 10) of the PCR amplicon after reverse sequencing (using reverse primer for sequencing), the sequence (SEQ ID NO: 8) of the designed hairpin construct, and the sequence (SEQ ID NO: 9) of the in silico BS DNA are aligned to calculate the BS-conversion rate.

FIG. 8 shows the nucleotide sequence alignment of SEQ ID NO: 8, SEQ ID NO: 9, and SEQ ID NO: 10. The arrows in FIG. 8 are the positions of methylated C. Table 7 shows the calculated BS-conversion rate of the forward sequence and the reverse complementary sequence (SEQ ID NO: 10). It may be seen from the results in Table 7 that the BS-conversion rates of the forward sequence and the reverse complementary sequence are both 100%.

TABLE 7

| Sequence | C->T (number) | C->C (number) | C->T (%) | C->C (%) | Number of C not originally methylated in sequencing region |
| --- | --- | --- | --- | --- | --- |
| Forward sequence | 62 | 0 | 100 | 0 | 62 |
| Reverse complementary sequence | 69 | 0 | 100 | 0 | 69 |

[Analysis of the Position of DNA Methylation Using Complementary Paired-End Sequencing]

In the present embodiment, the position of DNA methylation is analyzed using the following steps:
(1) sequence alignment is performed on the forward sequence (SEQ ID NO: 8) of the designed hairpin construct and the reverse complementary sequence (SEQ ID NO: 11) thereof;
(2) sequence alignment is performed on the forward sequence (SEQ ID NO: 9) of the in silico BS DNA and the reverse complementary sequence (SEQ ID NO: 12) thereof;
(3) the rules of DNA methylation are analyzed using "complementary paired-end sequencing";
(4) the sequence of the PCR amplicon after sequencing is analyzed using the above rules to restore the original DNA sequence and determine the position of methylated C.

[Sequence Alignment of the Forward Sequence of the Hairpin Construct and the Reverse Complementary Sequence Thereof]

Figure 9:
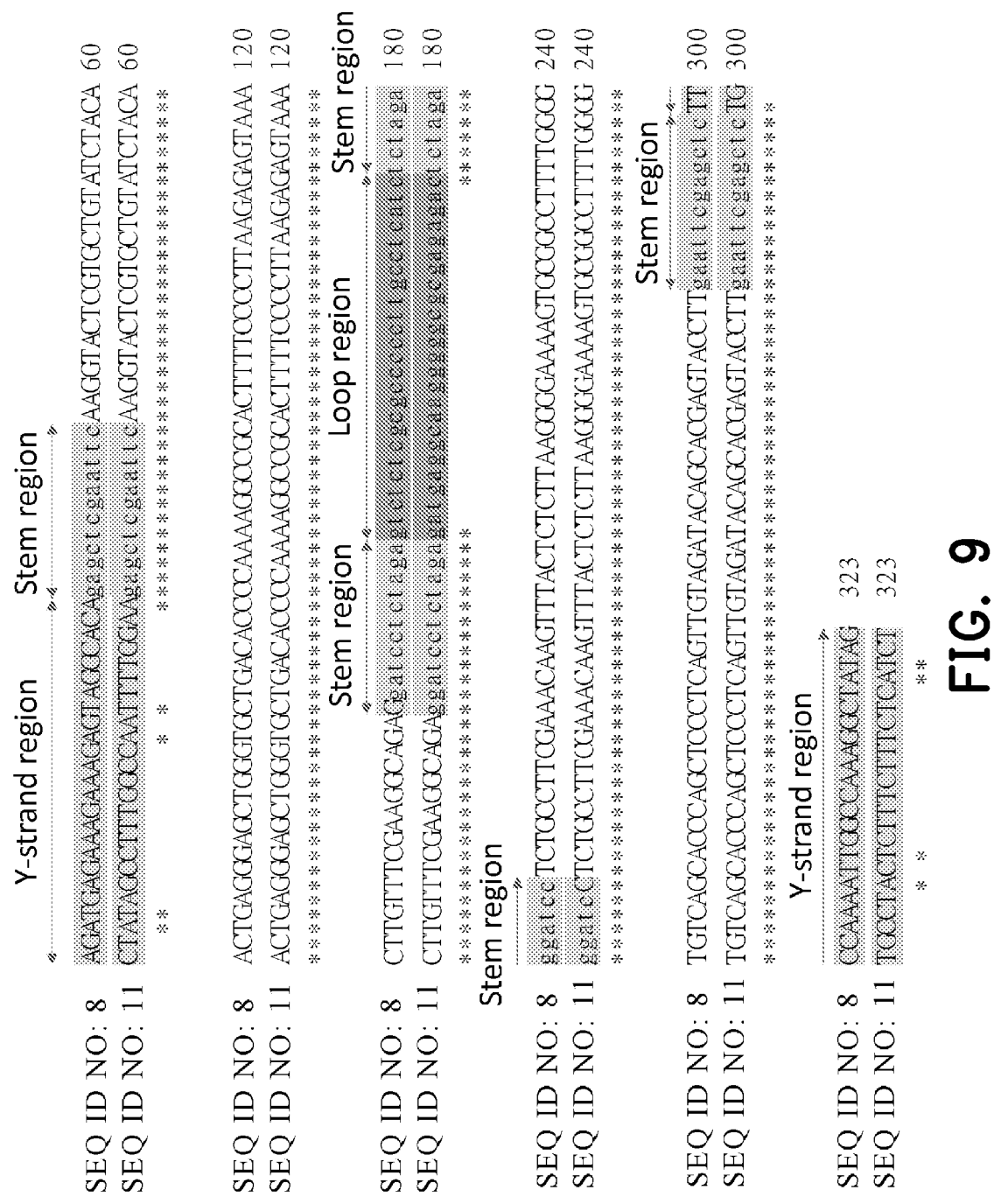

FIG. 9 shows the sequence alignment of the forward sequence of the designed hairpin construct and the reverse complementary sequence thereof. In FIG. 9, the forward sequence (SEQ ID NO: 8) of the hairpin construct represents "sequencing starting from the Y5 strand", and the reverse complementary sequence (SEQ ID NO: 11) of the hairpin construct represents "sequencing starting from the Y3 strand". It may be seen from FIG. 9 that the sequences (target double-stranded nucleic acid molecule and stem region) of the double-stranded DNA region are the same, and the sequences of the DNA regions of the single-stranded Y3 strand and the single-stranded Y5 strand are different, wherein the single-stranded Y3 strand indicates the sequence obtained from "sequencing starting from the Y3 strand", and the single-stranded Y5 strand indicates the sequence obtained from "sequencing starting from the Y5 strand".

[Sequence Alignment of the Forward Sequence of in Silico BS DNA and the Reverse Complementary Sequence Thereof]

Figure 10:
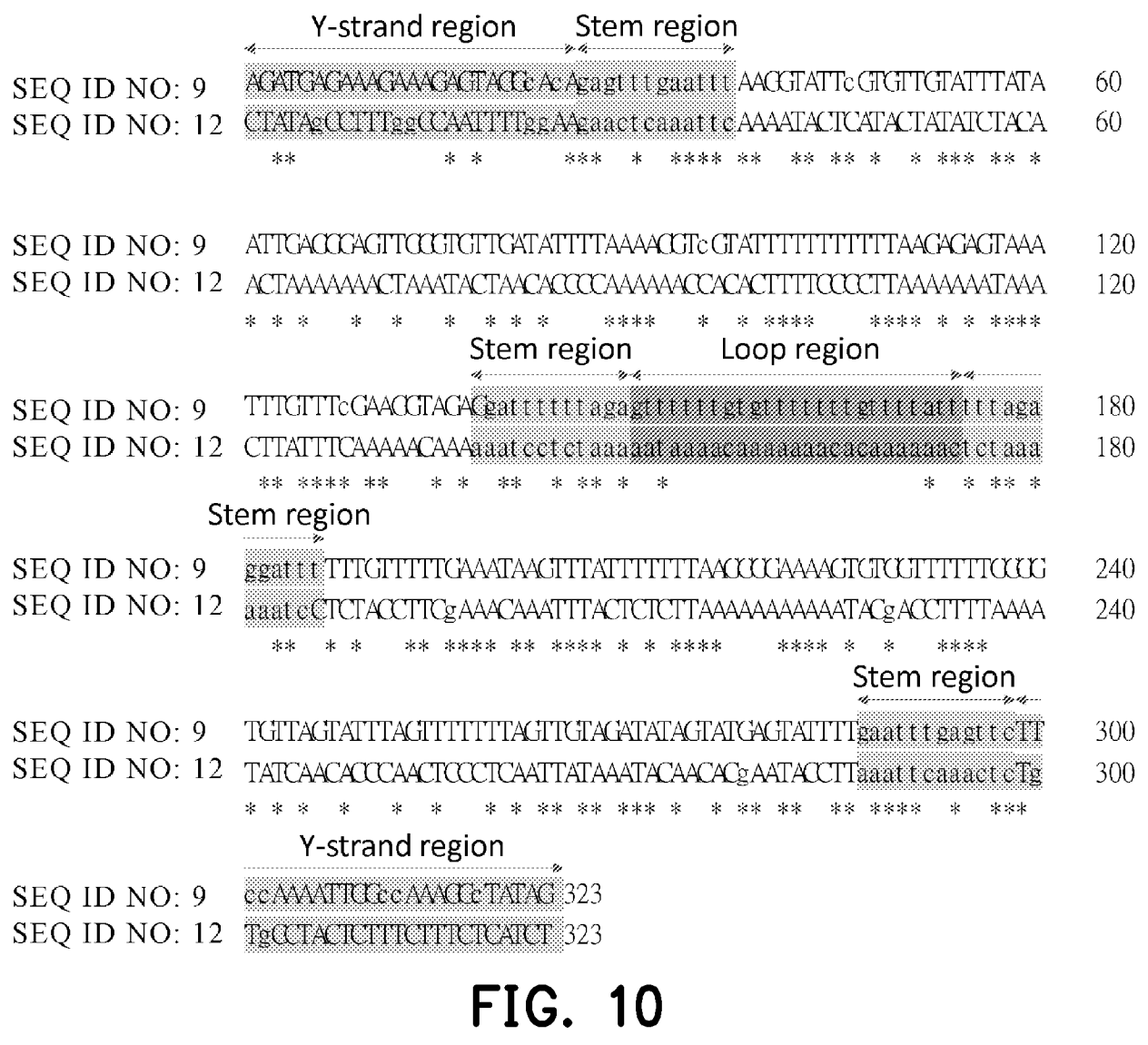

FIG. 10 shows the sequence alignment of the forward sequence of the hairpin construct of in silico bisulfate conversion and the reverse complementary sequence thereof. In FIG. 10, the forward sequence (SEQ ID NO: 9) of the in silico BS DNA represents "sequencing starting from the Y5 strand", and the reverse complementary sequence (SEQ ID NO: 12) of the in silico BS DNA represents "sequencing starting from the Y3 strand". It may be seen from FIG. 10 that in the sequences (target double-stranded nucleic acid molecule and stem region) of the double-stranded DNA region, the bases on the positions after bisulfite conversion are different, and the sequences of the DNA regions of the single-stranded Y3 strand and the single-stranded Y5 strand are different, wherein the single-stranded Y3 strand indicates the sequence obtained from "sequencing starting from the Y3 strand", and the single-stranded Y5 strand indicates the sequence obtained from "sequencing starting from the Y5 strand".

[Analysis of Rules of DNA Methylation Using "Complementary Paired-End Sequencing"]

Figure 11:
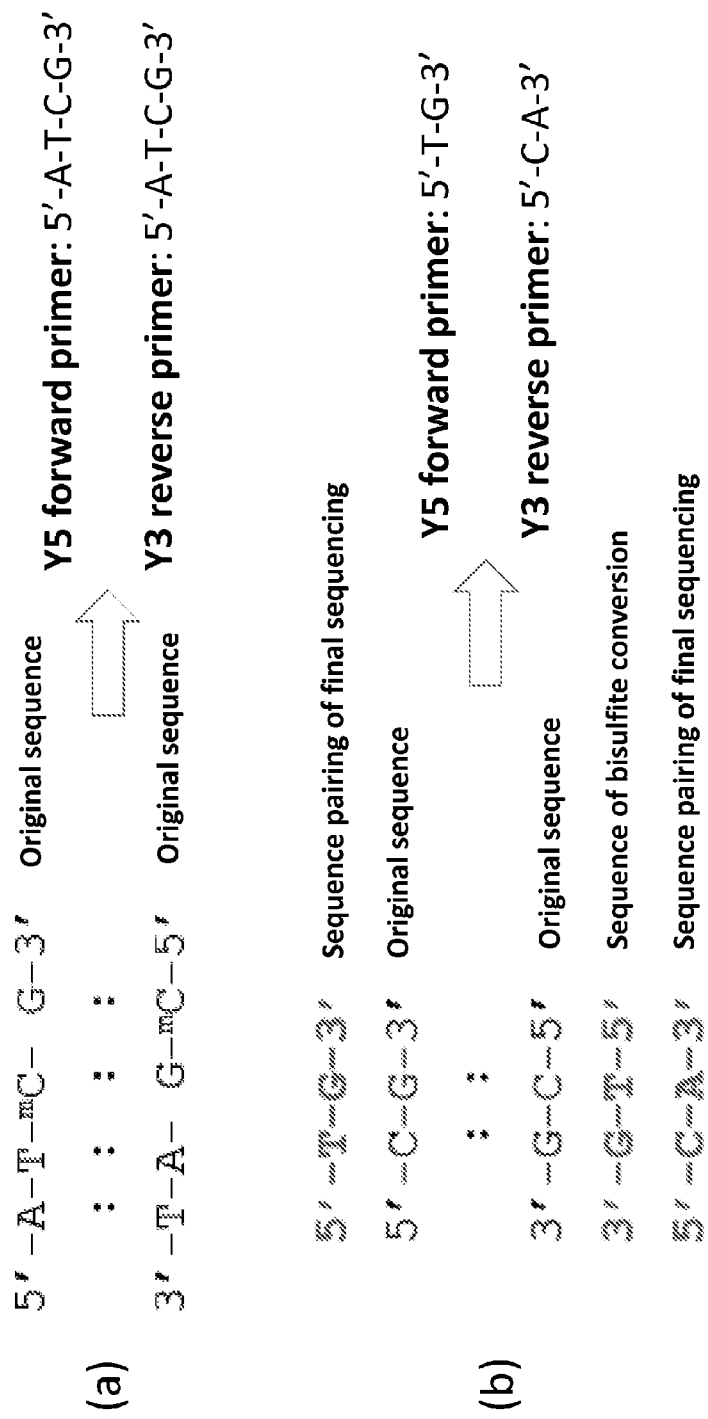
FIG. 11 shows the rules for analyzing DNA methylation.

Based on the sequence alignment data in FIG. 10, the rules of DNA methylation analysis may be obtained. FIG. 11 shows the rules for analyzing DNA methylation. Part (a) of FIG. 11 shows that C in the sequence is methylated and therefore is a base that is not converted by bisulfite. Therefore, the sequence of 5'-A-T-C-G-3' may be obtained regardless of whether sequencing is performed by the Y5 forward primer or the Y3 reverse primer. Part (b) FIG. 11 shows that C in the sequence is not methylated and is a base to be converted by bisulfite. Therefore, after bisulfite conversion, sequencing by the Y5 forward primer and the Y3 reverse primer results in specific base pairing (i.e., C-T and G-A).

[Analysis of the Sequence of PCR Amplicon after Sequencing Using the Above Rules to Restore the Original DNA Sequence and Determine the Position of Methylated C]

Sequence alignment is performed on the forward sequence (SEQ ID NO: 9) of in silico BS DNA, the reverse complementary sequence (SEQ ID NO: 12) of in silico BS DNA, the forward sequence (SEQ ID NO: 13) of the PCR amplicon after forward sequencing, and the reverse sequence (SEQ ID NO: 14) of the PCR amplicon after reverse sequencing. FIG. 12 shows the sequence alignment of SEQ ID NO: 9, SEQ ID NO: 12, SEQ ID NO: 13, and SEQ ID NO: 14.

According to the above analysis of DNA methylation rules, if there is a specific base pairing (i.e., C-T and G-A) on each base of each aligned sequence, the original DNA sequence may be restored according to the rules. The bases at the corresponding positions of each aligned sequence are all the same, indicating the corresponding position on the original DNA is the same base. For example, if the bases at the corresponding positions of four sequences are all A, it means that the base at the corresponding position of the original DNA is A. Therefore, according to the above rules, the methylation positions of the target nucleic acid molecule region in the hairpin construct may be determined, that is, there are 3 methylated cytosines at the positions indicated by the boxes in FIG. 12.

Based on the above, any strand of the PCR amplicon obtained by using the method of amplifying the target nucleotide sequence of the disclosure includes a forward target nucleotide sequence and a reverse target nucleotide sequence. Therefore, when nucleic acid sequencing is performed, sequencing from either end may produce the forward target nucleotide sequence and the reverse target nucleotide sequence. In addition, by aligning the resulting forward target nucleotide sequence and the reverse target nucleotide sequence with each other, the accuracy of restoring the original sequence may be improved. In addition, in the present embodiment, two complementary strands of DNA are held together for sequencing and analysis, so the cost of sequencing may be reduced.

It will be apparent to those skilled in the art that various modifications and variations may be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A method of amplifying a target nucleotide sequence, comprising the following steps:
    (a) linking a first adaptor and a second adaptor to two ends of a double-stranded nucleic acid molecule with a target nucleotide sequence respectively to form a nucleic acid template, wherein the target nucleotide sequence comprises a forward strand and a reverse strand, the first adaptor comprises a Y-form adaptor or a hairpin adaptor, and the second adaptor is a hairpin adaptor, wherein the first adaptor comprises a paired double-stranded part and an unpaired single-stranded part;
    (b) performing a denaturation reaction on the nucleic acid template;
    (c) performing a PCR amplification on the target nucleotide sequence, so that a first primer, a second primer, and a DNA polymerase are in contact with the nucleic acid template, wherein the first primer comprises a first sequence identical to a sequence of the single-stranded part of the first adaptor near the forward strand, and the second primer comprises a second sequence complementary to a sequence of the single-stranded part of the first adaptor near the reverse strand, and wherein the second primer binds to the single-strand part of the first adaptor and does not bind to the double-stranded part of the first adaptor; and
    (d) repeating step (c) to perform one or a plurality of PCR amplification cycles to obtain a PCR amplicon of the target nucleotide sequence.

2. The method of amplifying the target nucleotide sequence of claim 1, wherein performing the denaturation reaction on the nucleic acid template comprises performing a bisulfate treatment on the nucleic acid template.

3. The method of amplifying the target nucleotide sequence of claim 2, wherein a conversion rate of the bisulfate treatment is 60% or more.

4. The method of amplifying the target nucleotide sequence of claim 1, wherein the first adaptor is a hairpin adaptor,
    and wherein the single-stranded part comprises the sequence identical to the first sequence and the sequence complementary to the second sequence.

5. The method of amplifying the target nucleotide sequence of claim 1, wherein the first adaptor is a Y-form adaptor, and the single-stranded part comprises a first unpaired strand and a second unpaired strand, and wherein the first unpaired strand comprises the sequence identical to the first sequence, and the second unpaired strand comprises the sequence complementary to the second sequence.

6. The method of amplifying the target nucleotide sequence of claim 1, wherein the first adaptor is a hairpin adaptor, and the single-stranded part comprises at least one U base, wherein before step (b), the single-stranded part is digested at a position of the U base by uracil-DNA glycosylase and DNA glycosylase-lyase endonuclease VIII to form a first strand and a second strand, and wherein the first strand comprises the sequence identical to the first sequence, and the second strand comprises the sequence complementary to the second sequence.

7. The method of amplifying the target nucleotide sequence of claim 1, wherein the first adaptor is a hairpin adaptor, wherein the single-stranded part comprises the sequence identical to the first sequence and the sequence complementary to the second sequence, and the method further comprises performing an additional amplification on the nucleic acid template before step (c).

8. The method of amplifying the target nucleotide sequence of claim 7, wherein the additional amplification is a rolling circle amplification (RCA).

9. The method of amplifying the target nucleotide sequence of claim 8, wherein the RCA is a multiple primer RCA.

10. The method of amplifying the target nucleotide sequence of claim 8, wherein the RCA uses at least one complementary primer, and the complementary primer is complementary to the target nucleotide sequence.

11. The method of amplifying the target nucleotide sequence of claim 8, wherein the RCA uses at least one complementary primer, and the complementary primer is complementary to at least one of the first adaptor and the second adaptor.

12. The method of amplifying the target nucleotide sequence of claim 1, wherein the PCR amplicon of the target nucleotide sequence is used for a nucleic acid sequencing, and wherein the first adaptor comprises a sequence the same as or complementary to a first sequencing primer used for the nucleic acid sequencing and a sequence the same as or complementary to a second sequencing primer used for the nucleic acid sequencing, or the first primer comprises a sequence identical to the first sequencing primer, and the second primer comprises a sequence identical to the second sequencing primer.

13. The method of amplifying the target nucleotide sequence of claim 4, wherein the PCR amplicon of the target nucleotide sequence is used for a nucleic acid sequencing, and wherein the single-stranded part of the first adaptor comprises a sequence the same as or complementary to a first sequencing primer used for the nucleic acid sequencing and a sequence the same as or complementary to a second sequencing primer used for the nucleic acid sequencing, or the first primer comprises a sequence identical to the first sequencing primer, and the second primer comprises a sequence identical to the second sequencing primer.

14. The method of amplifying the target nucleotide sequence of claim 5, wherein the PCR amplicon of the target nucleotide sequence is used for a nucleic acid sequencing, and wherein the first unpaired strand comprises a sequence the same as or complementary to a first sequencing primer used for the nucleic acid sequencing, and the second unpaired strand comprises a sequence the same as or complementary to a second sequencing primer used for the nucleic acid sequencing, or the first primer comprises a sequence identical to the first sequencing primer, and the second primer comprises a sequence identical to the second sequencing primer.

15. The method of amplifying the target nucleotide sequence of claim 6, wherein the PCR amplicon of the target nucleotide sequence is used for a nucleic acid sequencing, and wherein the first strand comprises a sequence the same as or complementary to a first sequencing primer used for the nucleic acid sequencing, and the second strand comprises a sequence the same as or complementary to a second sequencing primer used for the nucleic acid sequencing, or the first primer comprises a sequence identical to the first sequencing primer, and the second primer comprises a sequence identical to the second sequencing primer.

16. The method of amplifying the target nucleotide sequence of claim 7, wherein the PCR amplicon of the target nucleotide sequence is used for a nucleic acid sequencing, and wherein the single-stranded part of the first adaptor comprises a sequence the same as or complementary to a first sequencing primer used for the nucleic acid sequencing and a sequence the same as or complementary to a second sequencing primer used for the nucleic acid sequencing, or the first primer comprises a sequence identical to the first sequencing primer, and the second primer comprises a sequence identical to the second sequencing primer.

17. The method of amplifying the target nucleotide sequence of claim 1, wherein the first adaptor comprises a nucleic acid marker or a barcode.

18. A method of determining a target nucleotide sequence, comprising:

providing the PCR amplicon of the target nucleotide sequence obtained by using the method of amplifying the target nucleotide sequence of claim 1;

performing a nucleic acid sequencing on the PCR amplicon of the target nucleotide sequence to obtain a sequence information of the target nucleotide sequence.

19. The method of determining the target nucleotide sequence of claim 18, further comprising preparing a sequencing DNA library using the PCR amplicon of the target nucleotide sequence before the nucleic acid sequencing is performed.

20. The method of determining the target nucleotide sequence of claim 18, wherein the nucleic acid sequencing is a next-generation sequencing.

* * * * *